(12) United States Patent
Wadhwa et al.

(10) Patent No.: US 7,883,702 B2
(45) Date of Patent: Feb. 8, 2011

(54) USE OF ANTI-MORTALIN 2 ANTIBODY AND FUNCTIONAL NUCLEIC ACID FOR CANCER THERAPIES

(75) Inventors: Renu Wadhwa, Ibaraki (JP); Kazunari Taira, Ibaraki (JP); Sunil Kaul, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 423 days.

(21) Appl. No.: 11/661,134

(22) PCT Filed: Aug. 25, 2005

(86) PCT No.: PCT/JP2005/015459

§ 371 (c)(1),
(2), (4) Date: Jun. 7, 2007

(87) PCT Pub. No.: WO2006/022344

PCT Pub. Date: Mar. 2, 2006

(65) Prior Publication Data

US 2008/0260739 A1    Oct. 23, 2008

(30) Foreign Application Priority Data

Aug. 26, 2004  (JP) .............................. 2004-246891
Aug. 24, 2005  (JP) .............................. 2005-242063

(51) Int. Cl.
*A61K 39/395*  (2006.01)
*C07K 16/30*  (2006.01)
*C07K 16/46*  (2006.01)

(52) U.S. Cl. .............. 424/141.1; 424/130.1; 424/133.1; 424/134.1; 424/135.1; 424/136.1; 424/138.1; 424/152.1; 424/155.1; 424/156.1; 424/172.1; 424/174.1; 530/387.1; 530/387.3; 530/387.7; 530/388.1; 530/388.8; 530/388.85; 530/391.3; 530/391.7

(58) Field of Classification Search .............. 424/130.1, 424/133.1, 134.1, 135.1, 136.1, 138.1, 141.1, 424/152.1, 155.1, 156.1, 172.1, 174.1; 530/387.1, 530/387.3, 387.7, 388.1, 388.8, 388.85, 391.3, 530/391.7
See application file for complete search history.

(56) References Cited

U.S. PATENT DOCUMENTS 5,627,039 A    5/1997  Pereira-Smith et al.

FOREIGN PATENT DOCUMENTS

JP    2001-354564 A    12/2001
WO    WO 2001/44807 A1    6/2001

OTHER PUBLICATIONS

Wadhwa, R. et al. Histol. Histopathol (2002) 17: 1173-1177.*
Wadhwa, R. et al., "Selective toxicity of MKT-077 to cancer cells is mediated by its binding to the Hsp70 family protein mot-2 and reactivation of p53 function." Cancer Res., 2000, p. 6818-21, vol. 60, No. 24.
Wadhwa, R. et al., "Identification of a novel member of mouse hsp70 family. Its association with Cellular mortal phenotype," J. Biol. Chem., 1993, p. 6615-21, vol. 268, No. 9. Kaul, Z. et al., "Mortalin imaging in normal and cancer cells with quantum dot immuno-conjugates," Cell Res., 2003, p. 503-7, vol. 13, No. 6.
Kanrei Murata et al., "RNA Kogaku kara no Ganchiryo eno Chosen", Igaku no Ayumi, Apr. 10, 2004, p. 119-120, vol. 209, No. 2.
Ui-Tei, K. et al., Guidelines for the selection of highly effective siRNA sequences for mammalian and Chick RNA interference. Nucleic Acids Res., Feb. 9, 2004, p. 936-48, vol. 32, No. 3.
Takano, S. et al., Elevated levels of mortalin expression in human brain tumors, Exp. Cell Res., 1997, p. 38-45, vol. 237, No. 1.
"Challenges of RNA Engineering for Cancer Therapy." Journal of Clinical and Experimental Medicine (Igaku no Ayumi), Apr. 10, 2004, p. 119-121, vol. 209, No. 2.

* cited by examiner

*Primary Examiner*—Alana M. Harris
*Assistant Examiner*—Anne L Holleran
(74) *Attorney, Agent, or Firm*—Sughrue Mion, PLLC

(57) ABSTRACT

The present invention relates to cancer therapies using an antibody that binds to mortalin 2 and a functional nucleic acid. Mortalin expression was found to be upregulated in immortalized cells and tumor tissues. Immortalized human cells highly expressing mortalin showed anchorage-independent growth. When the K antibody, which is a specific anti-mortalin antibody, was injected into a tumor of a nude mouse, tumor growth was suppressed or the tumor shrank compared with the case of a control. In accordance with the present invention, the use of a specific anti-mortalin antibody (K antibody) for tumor therapies and the use of such antibody as a carrier molecule for transportation of immunotoxicin and the like into cells are provided. It has been shown that mortalin can be a target for cancer therapies. In accordance with the present invention, a novel and effective anticancer agent is provided. In addition, an anti-mortalin antibody that is internalized by cells is developed. Thus, various applications using such antibody are provided.

17 Claims, 20 Drawing Sheets

Fig. 10
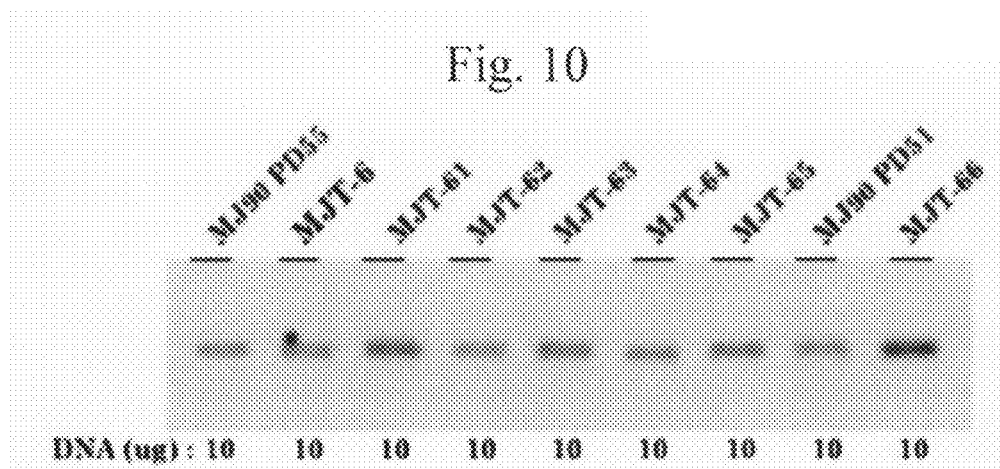
Fig. 11
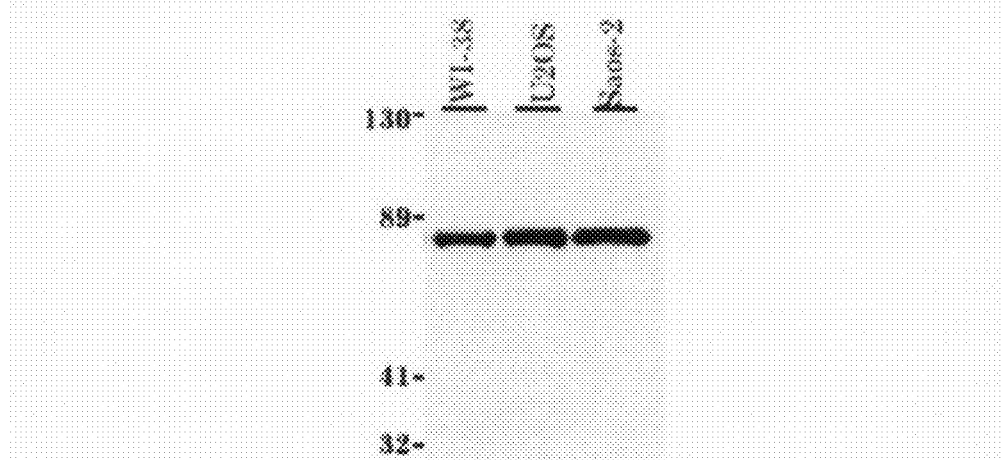
Fig. 12
Western with anti-V5 Ab

Normal cells    Cancer cells

TIG-1    U2OS    MCF7

40x magnification 100x magnification

Fig. 21

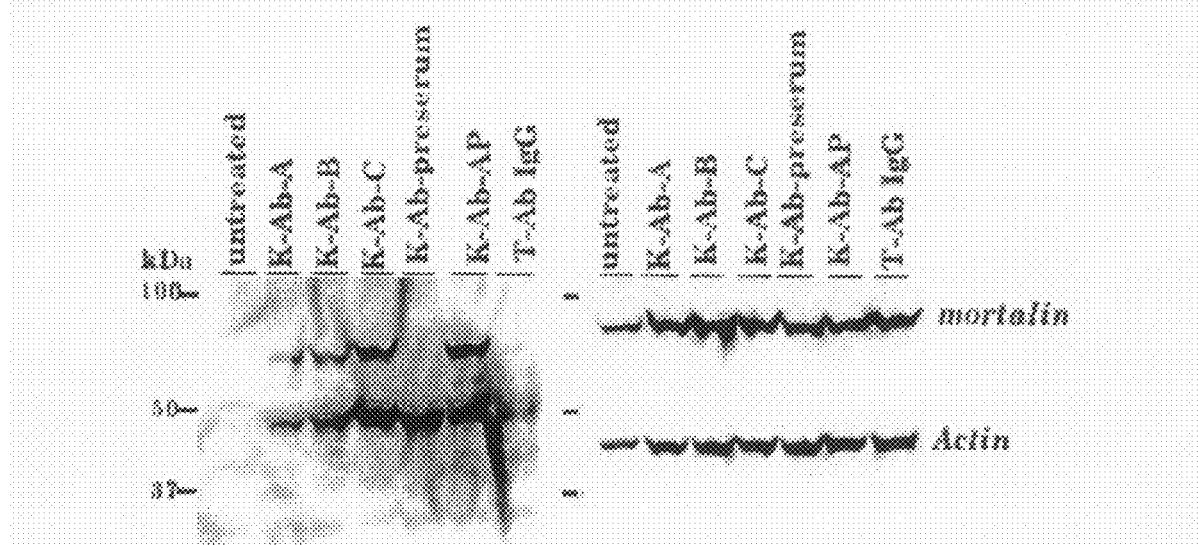

Fig. 22

Interleukin 1 receptor (type I) cDNA Seq and target sites for shRNA

'5- tagacgcacc ctctgaagal ggtgactccc tcctgagaag ctggaccect tggtaaaaga caaggcctc tccaagaaga atatgaaagt gttactcaga cttatttgtt tcatagctct actgattct tctctggagg ctgataaatg caaggaacgt gaagaaaaaa taatttagt gtcatctgca aatgaaattg atgttcgtcc ctgtcctctt aacccaaatg aacacaaagg cactataact tggtataaag atgacagcaa gacacctgtatctacagaac aagcctccag gattcatcaa cacaagaga aactttggtt tgttcctgct aaggtggagg attcaggaca ttactattgc gtggtaagaa attcatctta ctgcctcaga attaaaataa gtgcaaaatt shRNA1 289-307
5'-cacc ACAAGTCTCAGGATTCAT gtgtgtgc ATGAATCCTGGAGGCTTGT mm-3 shRNA2 293-311
5'-cacc GCTTCAGGATTCATCAAC gtgtgtgc GTTGATGAATCCTGGAGGC mm-3

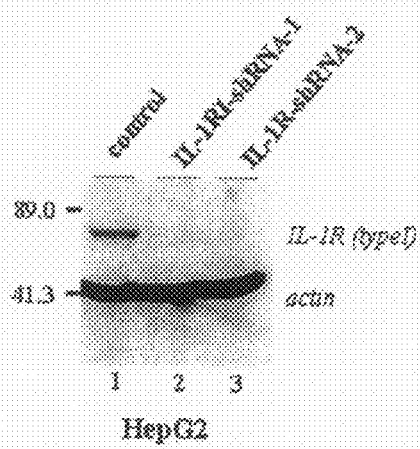

HepG2

Fig. 24

| Clone Name | Reactivity in Western | Reactivity in immuno-staining | Internalization |
|---|---|---|---|
| 1 | + | | |
| 3 | | | |
| 4 | ++ | +++ | |
| 5 | | | |
| 8 | ++ | + | |
| 9 | ++ | | |
| 11 | ++ | | |
| 14 | ++ | + | + |
| 15 | ++ | + | + |
| 19 | ++ | | |
| 20 | | | |
| 21 | + | + | + |
| 22 | + | | |
| 25 | ++ | ++++ | + |
| 29 | ++ | + | + |
| 30 | ++ | | |
| 31 | ++ | + | |
| 32 | | | |
| 34 | | | |
| 35 | ++ | | |
| 37 | ++ | ++++ | +++ |
| 38 | ++ | ++++ | +++ |
| 41 | ++ | | |
| 44 | ++ | | |
| 45 | ++ | +++ | ++ |

| Clone Name | Reactivity in Western | Reactivity in immuno-staining | Internalization |
|---|---|---|---|
| 46 | ++ | + | |
| 47 | ++ | +++ | + |
| 48 | ++ | + | + |
| 52 | ++ | +++ | |
| 58 | ++ | + | |
| 59 | | | |
| 61 | ++ | | |
| 63 | ++ | + | |
| 71 | ++ | ++++ | +++ |
| 76 | ++ | | |
| 75 | ++ | | |
| 77 | ++ | ++ | |
| 79 | ++ | +++ | |
| 86 | ++ | | |
| 87 | ++ | | |
| 93 | ++ | +++ | |
| 96 | ++ | ++++ | +++ |
| 99 | | | |
| 105 | ++ | + | |
| 109 | ++ | ++++ | ++ |
| 110 | | | |
| 112 | ++ | +++ | |
| 113 | | | |
| 115 | ++ | + | |

Fig. 25

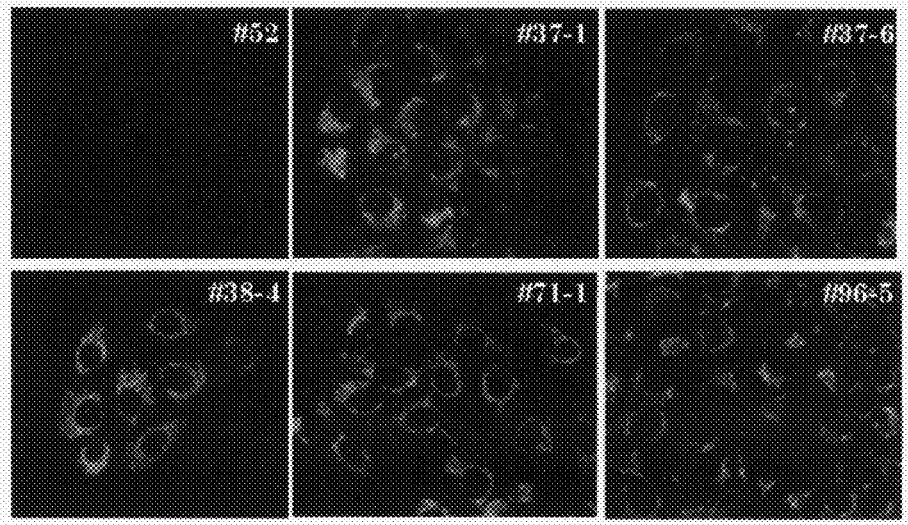

Internalized monoclonal Ab clones (24 h incubation): staining with FITC-conjugated mouse antibody

Fig. 26

|  | Acid wash | PBS wash |
|---|---|---|
| control | - | - |
| No.37-1 | ++ | ++ |
| No.37-6 | +++ | +++ |
| No.96-5 | ++ | ++ |
| No.52-3 | - | - |

Fig. 27

| MAM clone # | Internalization | | | |
|---|---|---|---|---|
| | U2OS (cancer cells) | | TIG-1 (Normal cells) | |
| | -anti-IL1R Ab | +anti-IL1R Ab | -anti-IL1R Ab | +anti-IL1R Ab |
| 37-1 | ++ | ++++ | - | - |
| 37-6 | ++ | ++++ | + | + |
| 38-4 | ++ | ++++ | - | - |
| 71-1 | + | + | - | - |
| 96-5 | + | + | - | - |
| 52-3 | - | - | - | - |
| Control | - | - | - | - |

37-1    37-6    38-4

| MAM clone # | Internalization | |
|---|---|---|
| | HepG2 (cancer cells) | TIG-1 (Normal cells) |
| Control | - | - |
| 37-6 | + | +/- |
| 37-6 + anti-IL1R Ab | ++ | + |
| 37-6 + anti-IL1R Ab IL-1R shRNA-1 | +++ | + |
| 37-6 + anti-IL1R Ab IL-1R shRNA-2 | +++ | + |
| 96-5 | + | +/- |
| 96-5 + anti-IL1R Ab | ++ | + |
| 96-5 + anti-IL1R Ab IL-1R shRNA-1 | +++ | + |
| 96-5 + anti-IL1R Ab IL-1R shRNA-2 | +++ | + |

USE OF ANTI-MORTALIN 2 ANTIBODY AND FUNCTIONAL NUCLEIC ACID FOR CANCER THERAPIES

TECHNICAL FIELD

The present invention relates to cancer therapies using an antibody that binds to mortalin 2 (mot-2) and also relates to a functional nucleic acid.

BACKGROUND ART

In view of the progress in biotechnology and cancer therapies, it is important to elucidate mechanisms involved in cell division control and immortalization. There is a limitation to the number of cell divisions in the cases of normal cells. Ultimately, cells reach a metabolically active state that is referred to as replicative senescence, or, in other words, permanent growth arrest (Non-Patent Document 33). However, when genetic or epigenetic changes are induced by certain mechanisms, it becomes possible for cells to continue to be divided permanently in culture while escaping the limitations of division capacity. This can be referred to as a state of cell "immortalization." In a very few cases, cells may spontaneously be immortalized. Control of the initiation and the termination of cell division at the molecular level have not so far been completely elucidated. For instance, when a viral oncogene is expressed in cells, the cell lifespan is extended. Then, such cells enter a stage that is referred to as "crisis." Very rarely (at an incidence of $10^{-9}$ to $10^{-6}$), few cells can escape from such "crisis" and become immortalized. Molecular basis of the phenomena such as, cell immortalization, malignant transformation, and tumor growth or development have not been elucidated. Although studies on the involvement of intracellular factors such as telomerase in the phenomena have been gaining attention, there are many studies suggesting that immortalization may take place by telomerase-independent telomere maintenance. These studies have suggested the existence of a certain senescence mechanism that is unrelated to telomeres, and the role of genes or routes that are independent from telomerase activity (Non-Patent Documents 34-38).

Mortalin is a protein involved in a variety of intracellular functions such as intracellular signal transduction, cell differentiation, and cell division control. A gene encoding mortalin was first isolated as an hsp 70 family protein present in the cytoplasmic fraction of a normal mouse fibroblast (Non-Patent Document 1). Subsequently, it has been revealed that such protein does not exist in the cytoplasmic fraction of an immortalized fibroblast. An antibody against a full-length mortalin protein that had been isolated from a normal fibroblast was produced (Non-Patent Document 1), and the resulting antibody was used for immunofluorescent staining. As a result, the staining was detected in the cytoplasm in normal cells. On the other hand, in the immortalized cells the staining was detected in the perinuclear region (Non-Patent Document 2).

Further, based on immunocloning of cDNA from a mouse-immortalized cell and comparison of that with the sequence isolated from a normal cell, it was revealed that two types of mortalin genes (mot-1 and mot-2) encoding different proteins exist. The proteins differ from each other only in 2 amino acid residues in the carboxyl terminal (Non-Patent Document 3). mot-1 (mortalin-1) exists in normal and mot-2 (mortalin 2) exists in immortalized cells.

Studies using NIH 3T3 cells have revealed that cDNAs of these two genes have contrasting biological activities. It has been revealed that the expression of mot-1 (mortalin 1) results in the generation of a cell-senescence-like phenotype. On the other hand, it has been revealed that, based on nude mouse assay, the overexpression of mot-2 (mortalin 2) causes malignant transformation (Non-Patent Document 4).

In the beginning of the mortalin study, it was not revealed whether mot-1 and mot-2 would be two different genes or alleles of each other (Non-Patent Documents 5 and 6). The ultimate answer was obtained based on mouse family study. Since it was found that two gene loci had been separated in mice in two generations, it became clear that mot-1 and mot-2 are alleles in the same loci in a mouse (Non-Patent Document 7).

Mortalin 2 was also identified as PBP74 (Non-Patent Document 8) mtHSP70 (Non-Patent Document 9), and GRP75 (Non-Patent Document 10). It has been remarked that mortalin 2 is involved in various functions related to stress response (Non-Patent Documents 10-15), intracellular transport (Non-Patent Document 11), antigen processing (Non-Patent Document 8), cell growth control (Non-Patent Documents 3, 4, and 12), control of in vivo nephrotoxicity (Non-Patent Documents 13 and 14), differentiation (Non-Patent Document 15) tumorigenesis (Non-Patent Documents 4 and 16), and so on.

In particular, mortalin 2 has been confirmed to bind to p53, a tumor suppressor protein, such that mortalin 2 inactivates the transcriptional activity of p53 (Non-Patent Document 17). Such p53 inactivation has been considered to be one of the causes of NIH 3T3 malignant cell transformation (Non-Patent Document 4) and lifespan prolongation of normal human fibroblast (Non-Patent Document 18). In addition, mortalin 2 has been found to cooperate with telomerase to immortalize a human foreskin fibroblast (Non-Patent Document 19).

In contrast with murine cells, human cells contain only one type of mortalin. Human mortalin has activity similar to that of murine mortalin 2 (mot-2), and thus it was referred to as hmot-2 (Non-Patent Document 4). In both mice and human cells, mortalin exists at multiple intracellular sites. Thus, it has been suggested that there are at least two types of mechanisms that are responsible for localized intracellular distribution of mortalin proteins (Non-Patent Document 20). The first mechanism is established based on the existence of different types of cDNAs, involving two alleles that have been found in mice (mot-1 and mot-2).

The second mechanism may involve unknown protein modifiers or cell factors to be found in both mice and humans.

In both the cases of humans and mice, upon detection of mortalin by staining with an antibody, the distribution of mortalin was confirmed throughout the cytoplasm in the case of normal cells, and in the cases of immortalized and tumor cells, it was localized to the perinuclear region. A human cell derived from an in vitro mutated tumor exhibits a mortalin staining pattern in which the distribution is not observed throughout the cytoplasm. However, a normal cell exhibits a staining pattern in which the distribution is observed throughout the cytoplasm (Non-Patent Document 21). When cell senescence was induced by introducing chromosome 7 into an SUSM1 cell, the mortalin staining pattern changed from the non-pancytoplasmic to the pancytoplasmic (Non-Patent Document 22). Also, in the case of induction of cell senescence with the use of 5-bromodeoxyuridine, similar changes in mortalin staining patterns have been observed (Non-Patent Documents 12 and 23). When human mutated cells experienced growth arrest by rhodacyanin dye treatment, changes in mortalin staining patterns were also observed (Non-Patent Document 24). Based on these studies, it has been shown that mortalin intracellular distribution is related to a phenotype for cell division.

Also, there are studies suggesting correlation between the mortalin expression level and the muscle or mitochondrial activity and differentiation (Non-Patent Documents 25 and 26). For instance, human mutated cells or tumor cell lines exhibit upregulation of mortalin expression (4). At the same time, mortalin expression level decreases during induction of differentiation in HL-60 promyelocytic leukocytes, (15). On the other hand, in mortalin-overexpressing cells, the level of differentiation induction was significantly reduced (Non-Patent Document 15).

Ssc1p is a homolog of mortalin in yeasts. Ssc1p is essential for cell viability (Non-Patent Document 27). In particular, Ssc1p has a function that is indispensable for mitochondrial transport (Non-Patent Document 28). Ssc1p is an essential constituent of a mitochondria transport apparatus, which binds to Tim-44, which is an inner mitochondrial membrane anchor (Non-Patent Documents 29 and 30). Mutations in Tim-44 that results in insufficient recruitment of mtsp70/Ssc1 are lethal to yeast cells (*Saccharomyces cerevisiae*) (Non-Patent Document 28). Based on studies of yeasts, mortalin has been estimated to have at least 3 types of activities. The activities include (i) unfolding of an extramitochondrial protein, (ii) one-way mitochondrial transmembrane transportation initiated by membrane potentials (M, $\Delta$, and $\Psi$), and (iii) completion of transfer through action as an ATP-driving motor. Also, mortalin is necessary for intramitochondrial degradation of a misfolded peptide with m-AAA and PIM1 proteases. In addition, it has been suggested that mortalin cooperates with mtHSP60 and CPN10 chaperones intramitochondrially, so as to fold a transferred protein such that the protein is formed into a functionally useful form, and that mortalin is involved in unknown functions of mtHSP60 in the extramitochondrial environment (Non-Patent Documents 31 and 32). Based on these reports, in addition to inactivation of tumor suppressor p53, functions of mortalin serving as a mitochondria transport apparatus and as chaperonine are expected to contribute to cell division phenotypes. Mortalin is considered to be a protein that is responsible for a variety of functions that control cell division at different intracellular sites.

A novel anticancer agent has been awaited, such agent should target the molecules that are characteristic of cancer cells and are involved in cancer cell division, immortalization, and metastasis. Such agents should have little adverse effects on normal cells. In addition, the development of target therapies has also been awaited, whereby adverse effects caused by destruction of normal cells can be avoided by allowing drugs such as anticancer agents, which have strong effects of incidentally killing normal cells, to have the property of being delivered to cancer cells in lesions so as to attack such cancer cells.

Antibody medicines are promising as new anticancer agents that are expected to achieve the above objectives. With the use of antibodies against antigen proteins of cancer cells to be eliminated it is possible to attack the cancer cells exclusively in affected parts. In addition, it is also possible to use the antibody medicines for target therapies for delivering drugs against target antigens. It is expected that such target therapies exert high levels of therapeutic effects.

Patent Document 1: JP Patent Publication (Kokai) No. 2001-354564 A

Patent Document 2: JP Patent Application No. 11-272778

Patent Document 3: JP Patent Application No. 11-357545

Non-Patent Document 1: Wadhwa, R., Kaul, S. C., Ikawa, Y., and Sugimoto, Y. (1993) J Biol Chem 268, 6615-6621

Non-Patent Document 2: Wadhwa, R., Kaul, S. C., Mitsui, Y., and Sugimoto, Y. (1993) Exp Cell Res 207, 442-448

Non-Patent Document 3: Wadhwa, R., Kaul, S. C., Sugimoto, Y., and Mitsui, Y. (1993) J Biol Chem 268, 22239-22242

Non-Patent Document 4: Kaul, S. C., Duncan, E. L., Englezou, A., Takano, S., Reddel, R. R., Mitsui, Y., and Wadhwa, R. (1998) Oncogene 17, 907-911

Non-Patent Document 5: Michikawa, Y., Baba, T., Arai, Y., Sakakura, T., Tanaka, M., and Kusakabe, M. (1993) Biochem Biophys Res Commun 196, 223-232

Non-Patent Document 6: Wadhwa, R., Akiyama, S., Sugihara, T., Reddel, R. R., Mitsui, Y., and Kaul, S. C. (1996) Exp Cell Res 226, 381-386

Non-Patent Document 7: Kaul, S. C., Duncan, E., Sugihara, T., Reddel, R. R., Mitsui, Y., and Wadhwa, R. (2000) DNA Res 7, 229-231

Non-Patent Document 8: Domanico, S. Z., DeNagel, D. C., Dahlseid, J. N., Green, J. M., and Pierce, S. K. (1993) Mol Cell Biol 13, 3598-3610

Non-Patent Document 9: Webster, T. J., Naylor, D. J., Hartman, D. J., Hoj, P. B., and Hoogenraad, N. J. (1994) DNA Cell Biol 13, 1213-1220

Non-Patent Document 10: Merrick, B. A., Walker, V. R., He, C., Patterson, R. M., and Selkirk, J. K. (1997) Cancer Lett 119, 185-190

Non-Patent Document 11: Mizukoshi, E., Suzuki, M., Loupatov, A., Uruno, T., Hayashi, H., Misono, T., Kaul, S. C., Wadhwa, R., and Imamura, T. (1999) Biochem J 343, 461-466

Non-Patent Document 12: Michishita, E., Nakabayashi, K., Suzuki, T., Kaul, S. C., Ogino, H., Fujii, M., Mitsui, Y., and Ayusawa, D. (1999) J Biochem 126, 1052-1059

Non-Patent Document 13: Bruschi, S. A., and Lindsay, J. G. (1994) Biochem Cell Biol 72, 663-667

Non-Patent Document 14: Bruschi, S. A., West, K. A., Crabb, J. W., Gupta, R. S., and Stevens, J. L. (1993) J Biol Chem 268, 23157-23161

Non-Patent Document 15: Xu, J., Xiao, H. H., and Sartorelli, A. C. (1999) Oncol Res 11, 429-435

Non-Patent Document 16: Takano, S., Wadhwa, R., Yoshii, Y., Nose, T., Kaul, S. C., and Mitsui, Y. (1997) Exp Cell Res 237, 38-45

Non-Patent Document 17: Wadhwa, R., Shyichi, T., Robert, M., Yoshida, A., Reddel, R. R., Nomura, H., Mitsui, Y., and Kaul, S. C. (1998) J Biol Chem 273, 29586-29591

Non-Patent Document 18: Kaul, S., Reddel, R. R., Sugihara, T., Mitsui, Y., and Wadhwa, R. (2000) in FEBS Letters Vol. 474, pp. 159-164

Non-Patent Document 19: Kaul, S. C., Yaguchi, T., Taira, K., Reddel, R. R., and Wadhwa, R. (2002) ECR submitted Non-Patent Document 20: Ran, Q., Wadhwa, R., Kawai, R., Kaul, S. C., Sifers, R. N., Bick, R. J., Smith, J. R., and Pereira-Smith, O. M. (2000) Biochem Biophys Res Commun 275, 174-179.

Non-Patent Document 21: Wadhwa, R., Pereira-Smith, O. M., Reddel, R. R., Sugimoto, Y., Mitsui, Y., and Kaul, S. C. (1995) Exp Cell Res 216, 101-106

Non-Patent Document 22: Nakabayashi, K., Ogata, T., Fujii, M., Tahara, H., Ide, T., Wadhwa, R., Kaul, S. C., Mitsui, Y., and Ayusawa, D. (1997) Exp Cell Res 235, 345-353

Non-Patent Document 23: Michishita, E., Nakabayashi, K., Ogino, H., Suzuki, T., Fujii, M., and Ayusawa, D. (1998) Biochemical And Biophysical Research Communications 253, 667-671

Non-Patent Document 24: Wadhwa, R., Sugihara, T., Yoshida, A., Nomura, H., Reddel, R. R., Simpson, R., Maruta, H., and Kaul, S. C. (2000) Cancer Res 60, 6818-6821

Non-Patent Document 25: Ibi, T., Sahashi, K., Ling, J., Marui, K., and Mitsuma, T. (1996) *Rinsho Shinkeigaku. Clinical Neurology* 36, 61-64

Non-Patent Document 26: Ornatsky, O. I., Connor, M. K., and Hood, D. A. (1995) Biochemical Journal 311 (Pt 1), 119-123

Non-Patent Document 27: Craig, E. A., Kramer, J., Shilling, J., Werner-Washburne, M., Holmes, S., Kosic-Smithers, J., and Nicolet, C. M. (1989) Mol Cell Biol 9, 3000-3008

Non-Patent Document 28: Merlin, A., Voos, W., Maarse, A. C., Meijer, M., Pfanner, N., and Rassow, J. (1999) J Cell Biol 145, 961-972

Non-Patent Document 29: Voos, W., von Ahsen, O., Muller, H., Guiard, B., Rassow, J., and Pfanner, N. (1996) Embo Journal 15, 2668-2677

Non-Patent Document 30: Krimmer, T., Rassow, J., Kunau, W. H., Voos, W., and Pfanner, N. (2000) Mol Cell Biol 20, 5879-5887

Non-Patent Document 31: Soltys, B. J., and Gupta, R. S. (2000) Int Rev Cytol 194, 133-196

Non-Patent Document 32: Soltys, B. J., and Gupta, R. S. (1999) Trends Biochem Sci 24, 174-177

Non-Patent Document 33: Hayflick, L., and Moorhead, P. S. (1961) Exp. Cell Res. 25, 585-621

Non-Patent Document 34: Bryan, T. M., Englezou, A., Dalla-Pozza, L., Dunham, M. A., and Reddel, R. R. (1997) Nat Med 3, 1271-1274

Non-Patent Document 35: Reddel, R. R. (1997) Jpn J Cancer Res 88, 1240-1241

Non-Patent Document 36: Wei, S., and Sedivy, J. M. (1999) Cancer Res 59, 1539-1543

Non-Patent Document 37: Oshimura, M., and Barrett, J. C. (1997) Eur J Cancer 33, 710-715

Non-Patent Document 38: Carman, T. A., Afshari, C. A., and Barrett, J. C. (1998) Experimental Cell Research 244, 33-42

DISCLOSURE OF THE INVENTION

It is an objective of the present invention to provide a new means for cancer therapies.

The present inventors have found that mortalin can be a useful target for cancer therapies. Thus, they have achieved the objective of providing a new means for cancer therapies with the use of reagents that target mortalin. In addition, they have found that there are some antibodies against mortalin that have capability of being internalized selectively into the cancer cells. Accordingly, they have devised a means of applying such antibodies to cancer therapies and other uses.

In view of usefulness of mortalin as a target for cancer therapies, the details of the present invention are described as follows.

(1) Mortalin is a useful target for cancer therapies. 1): Since the suppression of mortalin 2 protein expression and the neutralization of such protein are useful for cancer therapies, a means for i): neutralizing the mortalin 2 protein with an anti-mortalin 2 antibody and ii): suppressing the mortalin 2 protein expression with the use of functional nucleic acids (such as siRNA and shRNA) is provided. In addition, 2): it is possible to carry out screening of an anticancer substance with the use of the mortalin 2 protein. Further, 3): since there are differences between normal cells and cancer cells in terms of mortalin 2 protein localization, it is possible to differentiate between normal cells and cancer cells based on differences in terms of staining patterns that are obtained upon the use of an anti-mortalin 2 antibody, and thus, a detection kit is provided. The kit can be used for i): determining whether or not a test substance has an effect on cancer cells that induces conversion of cancer cells into normal cells or senescence cells and for ii): distinguishing normal cells and or cancer cells.

(2) There is an anti-mortalin 2 antibody having a capability of being internalized selectively by cancer cells, and thus, 1): such antibody can be used as a carrier. Also, i): it is possible to allow an anti-mortalin 2 antibody to carry a drug for use. Specifically, it is possible to use such antibody carrying a): a functional nucleic acid suppressing the expression of any oncogene as a drug or b): a (low molecular weight) compound suppressing the function of any protein as a drug. In addition, ii): it is possible to add a fluorescent substance or the like to an anti-mortalin 2 antibody for use. In such case, a): such antibody can be used for live imaging of cancer cells. In addition, it is also useful that 2): a capability of being internalized that is imparted to an anti-mortalin 2 antibody is promoted when the IL-1R type 1 expression is suppressed or IL-1R type 1 is neutralized.

In addition, another aspect of the present invention is described as follows, in view of an antibody against mortalin (anti-mortalin 2 antibody) and the use of the same. In particular, the antibody that has a capability of being internalized can be used for a variety of applications based on the internalization into live cells, for example, use of such antibody as a drug carrier for cancer cells and as a carrier used for live imaging of cancer cells. Alternatively, the antibody against mortalin, that has or does not have a capability of being internalized, can be used for a variety of applications based on its specific binding to mortalin. For instance, it can be used for distinguishing the normal cells and cancer cells in their staining patterns obtained by their immunostaining of immobilized cells with the anti-mortalin 2 antibodies.

The present inventors have found that the expression level of the mortalin gene is upregulated in most clinical tumor tissues and tumor cell lines, that it is possible to suppress tumor growth with the use of an antibody against a full-length mortalin 2 protein, and that such antibody is internalized by cells. This has led to the completion of the present invention.

Specifically, in accordance with the present invention, an anticancer agent comprising as an active ingredient a mortalin-2-neutralizing substance is provided. Further, in accordance with the present invention, an anticancer agent comprising as an active ingredient an antibody that binds to mortalin 2 is provided, such antibody being used as the mortalin-2-neutralizing substance. Herein, the antibody that binds to mortalin 2 may be an antibody against a full-length mortalin 2 protein or an antibody against a partial peptide comprising 5 or more amino acids of mortalin 2. In addition, the antibody that binds to mortalin 2 may be an antibody that is taken up into cells and then binds to mortalin 2.

Also, in accordance with the present invention, as the mortalin-2-neutralizing substance, a functional nucleic acid that targets any site comprising a transcriptional region and a promoter region of a mortalin-2 gene and an anticancer agent comprising, as an active ingredient, such functional nucleic acid are provided. Such functional nucleic acid may be siRNA, double stranded RNA, or siRNA or double stranded RNA, at least one strand of which is modified RNA.

Further, the present invention relates to a method for evaluating anticancer activity of a test substance with the use of mortalin, comprising any one of the following steps of:

(a) contacting a mortalin 2 protein with the test substance and then carrying out evaluation based on contact strength;

(b) contacting a cell in which an expression of mortalin 2 has been induced or a cell lysate thereof with the test substance, and then carrying out evaluation based on the contact strength; and (c) contacting a cell having DNA comprising a reporter gene ligated downstream of a promoter of a mortalin-2 gene or a cell lysate thereof with the test substance, and then carrying out evaluation using the expression of a reporter gene as an indicator.

Furthermore, in accordance with the present invention, a method for producing a pharmaceutical composition having anticancer activity, comprising a step of mixing a mortalin-2-neutralizing substance and a pharmaceutically acceptable carrier is provided. In one embodiment of such production method, the mortalin-neutralizing substance is an antibody that binds to mortalin 2. The antibody that binds to mortalin 2 may be an antibody against a full-length mortalin 2 protein or an antibody against a partial peptide comprising 5 or more amino acids of mortalin 2. In addition, the antibody that binds to mortalin 2 may be an antibody that is taken up into cells and then bind to mortalin 2. In another embodiment of the present invention, the mortalin-2-neutralizing substance can be a functional nucleic acid that targets any site comprising a transcriptional region and a promoter region of a mortalin-2 gene. Such functional nucleic acid may be siRNA, double stranded RNA, or siRNA or double-stranded RNA comprising a modified RNA strand as at least one strand thereof.

In addition, in accordance with the present invention, a method for producing a pharmaceutical composition having anticancer activity, comprising a step of mixing a substance that has been evaluated to have anticancer activity in accordance with the method for evaluating anticancer activity with the use of mortalin described above and a pharmaceutically acceptable carrier is provided.

In addition, in accordance with the present invention, the use of an anti-mortalin-2 antibody and a mortalin-2-binding substance as a carrier for intracellularly delivering immunotoxins, peptides, nucleotides, organic molecules, and other small molecules is provided.

In addition, in accordance with the present invention, the following artificial antibodies and a complex are provided:

an artificial antibody, which is a monomer of an antigen recognition site of an anti-mortalin-2 antibody or of a peptide that contains such antigen recognition site or a multimer such as a dimmer or a trimer of such monomer subjected to multimerization by chemical and genetic engineering techniques;

an artificial chimeric antibody, which is provided in the form a complex of an antigen recognition site of an anti-mortalin-2 antibody or a peptide that contains such antigen recognition site and another antibody, a part of another antibody, another protein, or the like based on chemical and genetic engineering techniques; and a complex, in which an antigen recognition site of an anti-mortalin-2 antibody or a peptide contains such antigen recognition site are bound to a substance that intracellularly delivers a drug, such as PEG (polyethylene glycol), liposome, or the like, and to a small molecule such as a radioactive substance, a toxin, or an anticancer agent.

Also, the present invention encompasses the following invention:

an anti-mortalin-2 antibody which is to be internalized by live cells, which is selected from the following (a) to (d):

(a) a polyclonal antibody that has been produced using a full-length mortalin-2 protein as an antigen;

(b) a polyclonal antibody that has been produced using a partial peptide comprising 5 or more amino acids of a mortalin 2 protein as an antigen;

(c) a monoclonal antibody that has been produced using a full-length mortalin 2 protein as an antigen; and (d) a monoclonal antibody that has been produced using a partial peptide comprising 5 or more amino acids of a mortalin 2 protein as an antigen;

wherein said antibody meets the following criteria of (1) to (3):

(1) having reactivity and specificity to mortalin 2 as determined by Western blotting analysis;

(2) exhibiting an immunostaining pattern of staining throughout the cytoplasm (pancytoplasmic staining) in the case of a normal cell and an immunostaining pattern of staining in the vicinity of the nuclear envelope (perinuclear staining) in the case of a cancer cell; and (3) being capable of being internalized by cells.

Such antibody is referred to as "an anti-mortalin 2 antibody having a capability of being internalized."

In addition, in other cases, an antibody with or without a capability of being internalized, that is produced using a partial peptide or a full-length peptide of a mortalin 2 protein as an antigen and specifically binds to a mortalin 2 protein is referred to as "antibody that specifically binds to mortalin 2.".

The inventions described below are provided with the use of antibodies described above.

An anticancer agent comprising, as an active ingredient, "the anti-mortalin 2 antibody having the capability of being internalized."

A method for transferring small molecules into cells, comprising using "the anti-mortalin 2 antibody having the capability of being internalized" as a carrier of the small molecules.

A method for promoting internalization of "the anti-mortalin 2 antibody having the capability of being internalized" by live cells, comprising a step of suppressing the expression of IL-1R type 1 or neutralizing IL-1R type 1.

The method described above, comprising suppressing the expression of IL-1R with the use of shRNA in the step of suppressing the expression of IL-1R type 1 or neutralizing IL-1R type 1.

Note that, specifically, shRNA may be, but not limited to, following (i) or (ii):

(i) wherein a target site sequence of shRNA is:

```
5'-ACA AGC CUC CAG GAU UCA U-3',
``` a shRNA corresponding to the target site 1), having the following sequence:

```
5'-ACA AGU CUC UAG GAU UCA UGU GUG CUG UCC AUG AAU
CCU GGA GGC UUG UUU-3';
or
```

(ii) wherein a target site sequence of shRNA is:

```
5'-GCC UCC AGG AUU CAU CAA C-3',
``` a shRNA corresponding to the target site 1), having the following sequence:

```
5'-GCU UUC AGG AUU CAU CAA CGU GUG CUG UCC GUU GAU
GAA UCC UGG AGG CUU-3'.
```

A kit for targeting therapies for cancer, comprising "the anti-mortalin 2 antibody having a capability of being internalized" combined with a substance having anticancer activity, wherein the anti-mortalin-2 antibody is used as a carrier of the substance having anticancer activity.

The kit for targeting therapies for cancer described above, further comprising a substance suppressing the expression of IL-1R type 1 or neutralizing IL-1R type 1, such substance being selected from a group consisting of antisense nucleotide, siRNA, shRNA, miRNA, double stranded RNA, a ribozyme, an antibody, and an antagonist.

A kit for live imaging of cancer cells, comprising a non-fluorescent or fluorescent substance visualizing "an anti-mortalin 2 antibody having a capability of being internalized" and a cancer cell for live imaging.

The kit for live imaging of cancer cells described above, further comprising a substance suppressing the expression of IL-1R type 1 or neutralizing IL-1R type 1, such substance being selected from a group consisting of antisense nucleotide, siRNA, shRNA, miRNA, double stranded RNA, a ribozyme, an antibody, and an antagonist.

A drug for therapies for cancer metastasis, comprising "the anti-mortalin 2 antibody having a capability of being internalized."

A method for detecting senescent or normalized cells in a cancer cell population or detecting cancer cells in a senescent or normalized cell population by differentiation between normal cells and cancer cells, comprising immunostaining with the use of "the antibody that specifically binds to mortalin 2."

A kit available for detecting senescent or normalized cells in a cancer cell population or for detecting cancer cells in a senescent or normalized cell population by differentiation between normal cells and cancer cells, containing "the antibody that specifically binds to mortalin 2," a reagent that is necessary for immunostaining, and an instruction.

A method for detecting senescent or normalized cells in a cancer cell population or cancer cells in a senescent or normalized cell population by differentiation between normal cells and cancer cells, comprising carrying out live imaging of cancer cells with the use of "the anti-mortalin 2 antibody having a capability of being internalized."

A kit available for detecting senescent or normalized cells in a cancer cell population or for detecting cancer cells in a senescent or normalized cell population by differentiation between normal cells and cancer cells, containing "the anti-mortalin 2 antibody having a capability of being internalized," a reagent that is necessary for live imaging, and an instruction.

A method for screening for a substance that transforms cancer cells into senescent or normalized cells by contacting a test substance with cancer cells, immunostaining the cancer cells with the use of "the antibody that specifically binds to mortalin 2," and observing immunostaining patterns, wherein if the immunostaining patterns are characteristic of senescent or normalized cells, the test substance is considered to be a substance that transforms cancer cells into senescent or normalized cells.

A kit available for screening for a substance that transforms cancer cells into senescent or normalized cells, comprising "the antibody that specifically binds to mortalin 2," a reagent that is necessary for immunostaining, and a instruction.

A method for screening for a substance that transforms cancer cells into senescent or normalized cells by comprising a test substance with cancer cells, carrying out live imaging of the cancer cells with the use of "the anti-mortalin 2 antibody having a capability of being internalized," and observing live imaging patterns, wherein if the live imaging patterns are characteristic of senescent or normalized cells, the test substance is considered to be a substance that transforms cancer cells into senescent or normalized cells.

A kit available for screening for a substance that transforms cancer cells into senescent or normalized cells, comprising "the anti-mortalin 2 antibody having a capability of being internalized," a reagent that is necessary for live imaging, and an instruction.

EFFECTS OF THE INVENTION

It has been demonstrated that mortalin can be a target for cancer therapies. In accordance with the present invention, a novel and effective anticancer agent is provided. In addition, an anti-mortalin antibody to be internalized by cells has been developed. Also, a variety of applications using such antibody are provided.

BRIEF DESCRIPTION OF THE DRAWINGS

FIG. 10 shows fingerprints of MJ90 and clones derived from MJ90 (Example 2).

FIG. 11 shows the results of Western blotting of human cells derived from a normal cell (WI-38) and tumor cells (U2OS and Saos-2) with the use of the mortalin-K antibody (Example 3).

FIG. 12 shows the results of mortalin immunoprecipitation with the use of the Mortalin-K antibody. U2OS cells were transfected with an expression plasmid encoding Mortalin-V5 protein. An immunoprecipitation reaction by using the Mortalin-K antibody (V5-tagged protein) was detected using an anti-V5-tag antibody by Western blotting (Western with anti-V5 Ab) (Example 3).

FIG. 21 shows the results of Western blotting for internalized K antibodies (Example 5).

FIG. 22 shows the suppression of the expression of interleukin-1 receptor type 1 (IL-1R type 1) (Example 6).

FIG. 24 shows production of a monoclonal antibody against mortalin and selection of an anti-mortalin monoclonal antibody having a capability of being internalized (Example 7).

FIG. 25 shows the detection of the monoclonal antibodies internalized by cells via immunostaining using an FITC-binding secondary antibody (Example 7).

FIG. 26 shows the confirmation of internalization of the anti-mortalin monoclonal antibody, following acid washing treatment of cells (Example 7).

FIG. 27 shows the selective internalization of the anti-mortalin monoclonal antibodies by cancer cells (Example 8).

Figure 1:
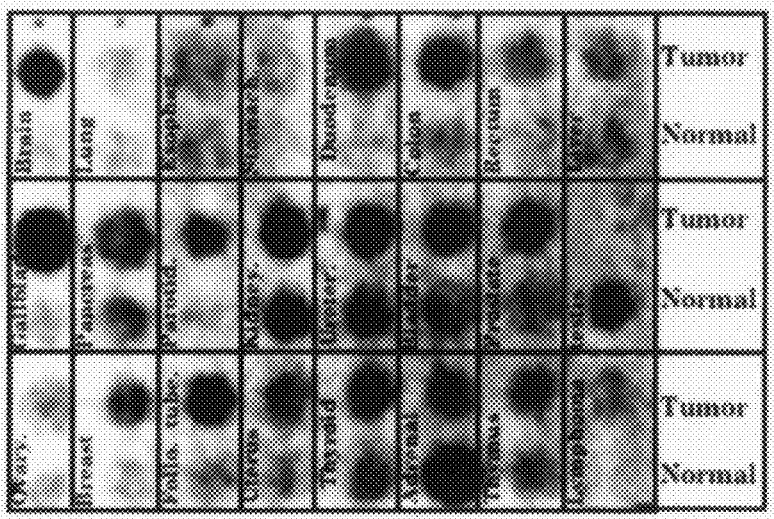
FIG. 1 shows the results of analyzing the dot blotting (each contains 2 μg of polyA RNA.) for the mortalin gene expression in various types of tumor tissues (Tumor) and the mached normal tissues (Normal) as controls. (Example 1).

BEST MODE FOR CARRYING OUT THE INVENTION (1) Mortalin-2 Gene and Protein

In the present invention, the term "mortalin" or "mortalin 2" refers to murine mortalin 2 (mot-2) or human mortalin (hmot-2), unless otherwise specified. These mortalins may be also simply referred to as "mortalin". Human mortalin has a function of causing cells to be malignantly transformed, as with the case of murine mortalin 2. The gene and protein of murine mortalin and those of human mortalin are known. The following reference contains the information about murine mortalin (mot-2): Wadhwa, R., Kaul, S. C., Ikawa, Y., and Sugimoto, Y. (1993) J Biol Chem 268, 6615-6621 (Non-Patent Document 1). Also, the following reference contains the information about human mortalin (hmot-2): Bhattacharyya, T. et al. Cloning and subcellular localization of human mitochondrial hsp70, J Biol Chem 270, 1705-10 (1995). Murine mortalin and human mortalin have more than 95% homology in terms of the protein level.

(2) Mortalin-2-Neutralizing Substance

The term "mortalin-2-neutralizing substance" means any substance capable of inhibiting intracellular functions of mortalin 2. As described above, mortalin 2 has a variety of intracellular functions. However, in the present invention, the function of inactivating tumor suppressor p53 and the function of controlling cell division are particularly important. Neutralization of mortalin 2 may be inhibition of a function of a mortalin protein or inhibition of mortalin gene expression. The inhibition of a function of a mortalin protein may be complete or partial inhibition. The inhibition of mortalin gene expression is inhibition of transcription and/or translation of the mortalin gene.

The present inventors have found that the expression and transcription levels of the mortalin gene are upregulated in most of the clinically derived tumor tissues and tumor cell lines. In addition, they have found that tumor growth is suppressed by injecting an antibody against mortalin 2 into tumors. By neutralizing mortalin 2 in tumor cells, intracellular functions of mortalin 2 are inhibited, so that it becomes possible to inhibit tumor cell growth.

(3) Antibody that Binds to Mortalin 2

In one embodiment of the present invention, an antibody that binds to mortalin 2 can be used as a mortalin-2-neutralizing substance. An antibody that is used in the present invention can be obtained as a polyclonal or monoclonal antibody with the use of a full-length protein or partial peptide of murine or human mortalin as an antigen according to conventional techniques for antibody production. As described above, since the murine mortalin protein and the human mortalin protein exhibit very high homology, an antibody raised against murine mortalin 2 recognizes a human mortalin protein, and vice versa.

A mortalin protein such as full-length mortalin proteins that have been isolated from murine cells or have been recombinantly produced and partial mortalin peptides that have been synthesized based on known amino acid sequences can be used as an antigen, as appropriate. When obtaining a monoclonal antibody alone, it is not always necessary to carry out purification of the antigen. However, when obtaining a polyclonal antibody, the antigen is purified by HPLC, SDS-PAGE, or the like.

A polyclonal antibody can be produced with a technique whereby an antibody is produced by immunizing a rabbit and collecting the blood thereof. The term "polyclonal antibody" in this context, means a centrifuged antiserum (IgG crude fraction). When it is desired to purify an antibody alone from such antiserum, purification can be carried out using a commercially available column filled with protein A or protein G and an affinity column in which mortalin proteins or peptides that serve as antigens are bound to appropriate carriers. The term "polyclonal antibody" used in the present invention includes an antiserum (IgG crude fraction) and a purified antibody.

A polyclonal antibody can be produced in the manner described below, for example. A rabbit is immunized with 1 to 1.5 mg of an antigen in 4 divided doses. Specifically, the antigen is prepared at an adequate protein concentration (1 mg/ml) with a saline solution (0.9 w/w % NaCl aqueous solution). The obtained solution is mixed with complete Freund's adjuvant at a volume ratio of 3:2 to produce a water-in-oil emulsion.

Each immunization is carried out at one week to 10 days intervals. For initial immunization, an antigen (in an amount equivalent to 0.5 mg/rabbit) is subcutaneously injected into a footpad or a flank of two New Zealand white rabbits (SPF (special pathogen free), 12 weeks old, female). For boost immunization, an antigen emulsion produced with an incomplete Freund's adjuvant in a similar manner (in amounts equivalent to 0.25 mg antigen per rabbit) are subcutaneously injected in divided doses into several sites of the backs of the rabbits. The boost immunizations are carried out 3 times. Approximately 10 days after the final immunization, whole blood is aseptically corrected from the ear artery or the carotid artery. The whole blood is centrifuged to separate the plasma.

Next, the obtained plasma is heat-treated in a hot bath at 56° C. for 30 minutes. Thereafter, an equal volume of 0.01 M PBS (−) buffer (0.01 M phosphate-buffered physiological saline (pH 7.4) containing 0.1% $NaN_3$) is added to the plasma at 2° C. to 15° C. for dilution. Then, an equal volume of a saturated ammonium sulfate aqueous solution (pH 7.4) pre-prepared in ammonia water, is added to the diluted solution. The resulting solution is treated with a high-speed refrigerated centrifuge (4° C., 30 minutes, 14000 rpm; 1000×G), followed by removal of the supernatant. A saline solution is added to the pellet and the pellet is completely dissolved. The resultant is subjected to dialysis or it is applied onto a Sephadex G25M column to remove remaining ammonium sulfate therefrom. Removal of ammonium sulfate is confirmed using a Nessler reagent (Nacalai Tesque). Thereafter, equal volumes of the internal dialysate and a cooled clarifying agent (Friegen, Behringwerke; trichlorotrifluoroethane) are mixed, followed by shaking and centrifugation, thereby isolating an internal solution phase therefrom. Such degreasing procedure is repeated 3 times to generate a crude IgG fraction (polyclonal antibody).

The present inventors produced 6 types of different polyclonal antibodies that bind to mortalin (against partial mortalin peptides as an antigen in 5 out of 6 types, and against a bacterially expressed full-length mortalin protein as an antigen in 1 out of 6 types). The present inventors have found that the antibody against the full-length protein (K antibody) that has been added to a culture solution is taken up into live cells; that is to say, the antibody is internalized by live cells. Also, the present inventors produced a monoclonal antibody against mortalin, and thus they have found an antibody has a similar capability of being internalized, among the monoclonal antibodies.

Such antibody that is internalized by live cells and then bound to mortalin is particularly preferred as an antibody that binds to mortalin for use in the present invention. In addition to its purpose of neutralizing mortalin, such antibody (anti-mortalin 2 antibody having a capability of being internalized) can be used as a carrier of small molecules into tumor cells. With the use of such antibody as a carrier, preferably, immunotoxicin, peptides, nucleotides, organic molecules, and other small molecules can be introduced into tumor cells.

In addition, the present inventors have found that intracellular internalization of an antibody is promoted when the expression of IL-1 receptor (type I), which is a receptor protein existing on the cell membrane surface, is suppressed.

The present inventors have established the following theory as a hypothesis regarding internalization. Although the present invention is not constrained by such theory, the theory is described herein as an aid to the understanding of the present invention.

In the case of a cancer cell, a mortalin 2 protein also exists on the cell membrane surface. When an anti-mortalin 2 antibody having a capability of being internalized is added to a cell culture solution, followed by cell culture, such anti-mortalin 2 antibody binds to a mortalin 2 protein on the cell membrane surface. The anti-mortalin 2 antibody-a mortalin 2 protein complex is transferred from the cell membrane into a cell. As a result, an anti-mortalin 2 antibody is internalized by such cell.

An IL-1 receptor (type 1) is a receptor protein existing on the cell membrane surface. In the case of a cancer cell, a mortalin 2 protein also exists on the cell membrane surface. Thus, IL-1R interacts with (binds to) a mortalin 2 protein on the cell membrane surface. Since an anti-mortalin 2 antibody cannot bind to a mortalin 2 protein binding to IL-1R, an anti-mortalin 2 antibody having the capability of being internalized cannot be transferred into a cancer cell. However, when interaction between IL-1R and a mortalin 2 protein is inhibited, free mortalin 2 proteins on cell membrane surfaces are increased. (For instance, as an inhibition method, suppression (knockdown) of IL-1R expression, neutralization of IL-1R on the cell membrane surface by adding an anti-IL-1R antibody to a culture solution, or the like is carried out.) Thus, an "anti-mortalin 2 antibody having a capability of being internalized" gets more opportunities to bind to a free mortalin 2 protein on the cell membrane surface, thereby intracellular internalization of the antibody is promoted.

A monoclonal antibody is more preferred than a polyclonal antibody in terms of stable production of homogenous antibodies. A monoclonal antibody can be prepared by any method for producing antibodies in a continuous cell culture system. Examples of such method include, but are not limited to, the following: the hybridoma method (Koehler and Milstein, (1975) Nature, 256, 495-497); the human B cell hybridoma method (Kosbor et al., (1983) Immunol. Today, 4, 72; Cote et al., (1983) Proc. Natl. Acad. Sci. (USA) 80, 2026-2030); and the EBV-hybridoma method (Cole et al., (1985) Monoclonal Antibody and Cancer Therapies, Alan R Liss, pp. 77-96). A monoclonal antibody-producing hybridoma can be produced as described below in accordance with, for example, the method of Milstein et al. (Kohler. G. and Milstein, C., Methods Enzymol. (1981) 73: 3-46). Specifically, a hybridoma can be produced by performing immunization with a desired antigen or a cell expressing a desired antigen as a sensitizing antigen according to usual immunization methods, fusing the obtained immunocytes with known parent cells according to usual cell fusion methods, and screening for monoclonal antibody-producing cells (hybridomas) according to usual screening methods.

In addition, upon hybridoma production, an antibody gene can be cloned from a hybridoma, inserted into an adequate vector, introduced into a host, and a recombinant antibody can be produced by genetic engineering techniques for use (see, for example, Carl, A. K. Borrebaeck, James, W. Larrick, THERAPEUTIC MONOCLONAL ANTIBODIES, Published in the United Kingdom by MACMILLAN PUBLISHERS LTD., 1990). Specifically, cDNA of a variable region (V region) of an antibody is synthesized from mRNA derived from a hybridoma with a reverse transcriptase. When DNA encoding an antibody V region of interest is obtained, such DNA is ligated to DNA encoding a desired antibody constant region (C region). The resultant is incorporated into an expression vector. Alternatively, DNA encoding an antibody V region may be incorporated into an expression vector containing DNA of an antibody C region. As an example, DNA is incorporated into an expression vector in a manner such that DNA is expressed under the control of an expression regulatory region, such as an enhancer or a promoter. Then, a host cell is transformed with such expression vector to express an antibody. Further, in order to obtain an antibody molecule having adequate antigen specificity and bioactivity, it is also desirable to construct a chimeric antibody. A chimeric antibody can be prepared by splicing a mouse antibody gene to a human antibody gene, for example, in accordance with the methods described in the following references: Morrison et al. (1984) Proc. Natl. Acad. Sci. (USA) 81, 6851-6855; Neuberger et al. (1984) Nature, 312, 604-608; Takeda et al. (1985) Nature, 314, 452-454. In addition, an anti-mortalin 2 antibody conjugated to various types of molecules such as polyethylene glycol (PEG) can be also used. Such modified antibody can be obtained by chemically modifying an obtained antibody in accordance with techniques established in the art. In such case, the antibody can be highly functionalized.

The antibody of the present invention includes an artificial antibody and a complex, each of which comprises an antigen recognition site of an anti-mortalin 2 antibody. That is, the antibody of the present invention includes: an artificial antibody, which is a monomer of an antigen recognition site of an anti-mortalin-2 antibody or of a peptide that contains such antigen recognition site, or a multimer such as a dimmer or a trimer of such monomer subjected to multimerization by chemical or genetic engineering techniques; and an artificial chimeric antibody, which is provided as a complex of an antigen recognition site of an anti-mortalin-2 antibody or a peptide that contains such antigen recognition site and another antibody, a part of another antibody, another protein, or the like based on chemical or genetic engineering techniques. In addition, a complex in which an antigen recognition site of an anti-mortalin-2 antibody or a peptide that contains such antigen recognition site are bound to a substance that intracellularly delivers a drug, such as PEG (polyethylene glycol), liposome, or the like, and to a small molecule such as a radioactive substance, a toxin, or an anticancer agent, can also be used in the present invention.

(4) Functional Nucleic Acid Targeting any Site of the Mortalin Gene

In another embodiment of the present invention, a functional nucleic acid can be used as a mortalin-neutralizing substance, such functional nucleic acid targeting any site comprising a transcriptional region and a promoter region of a mortalin-2 gene. Such functional nucleic acid is a nucleic acid molecule having the function of controlling the expression of a particular gene or the action of the gene product, such as siRNA, shRNA, miRNA, double stranded RNA, ribozyme, and antisense. With the use of such functional nucleic acid, it is possible to prevent gene expression and neutralize mortalin at the gene level. A person skilled in the art can design such functional nucleic acid on the basis of the known sequence information of mortalin 2 and, for example, the following references (Wadhwa, R., Kaul, S. C., Miyagishi, M., Taira, K. (2004) Know-how of RNA interference and its applications in research and therapies, Reviews in Mutat. Res. (in press); Wadhwa, R., Kaul, S. C., Miyagishi, M. and Taira, K. (2004) Vectors for RNA interference, Current Opinions in Molecular Therapeutics (in press); Wadhwa, R., Ando, H., Kawasaki, H., Taira, K., and Kaul, S. C. (2003); and Conventional and RNA helicase coupled hammerhead ribozymes for mortalin, EMBO Reports, 4, 595-601).

(5) Anticancer Agent Comprising, as an Active Ingredient, an Antibody that Binds to Mortalin 2

An anticancer agent comprising as an active ingredient an antibody that binds to mortalin 2 can be formulated in accordance with a conventional method (Remington's Pharmaceutical Science, latest edition, Mark Publishing Company, Easton, U.S.A.). Such agent may further comprise a pharmaceutically acceptable carrier or additive.

The anticancer agent of the present invention may contain a toxic agent. Examples of a toxic agent that can be used include polyethylene glycol and sugars such as dextran, mannitol, sorbitol, inositol, glucose, fructose, lactose, xylose, mannose, maltose, and raffinose.

The anticancer agent of the present invention may further contain a surfactant. Typical examples of such a surfactant include: nonionic surfactants, including sorbitan fatty acid esters such as sorbitan monocaprylate, sorbitan monolaurate, and sorbitan monopalmitate, glycerin fatty acid esters such as glycerin monocaprylate, glycerin monomyritate, and glycerin monostearate, polyglycerin fatty acid esters such as decaglyceryl monostearate, decaglyceryl distearate, and decaglyceryl monolinolate, polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate, polyoxyethylene sorbit fatty acid esters such as polyoxyethylene sorbit tetrastearate and polyoxyethylene sorbit tetraoleate, polyoxyethylene glycerin fatty acid esters such as polyoxyethylene glyceryl monostearate, polyethylene glycol fatty acid esters such as polyethylene glycoldistearate, polyoxyethylene alkyl ethers such as polyoxyethylene lauryl ether, polyoxyethylene polyoxypropylene alkyl ethers such as polyoxyethylene polyoxypropylene glycol ether, polyoxyethylene polyoxypropylene propyl ether, and polyoxyethylene polyoxypropylene cetyl ether, polyoxyethylene alkyl phenyl ethers such as polyoxyethylene nonyl phenyl ether, polyoxyethylene cured castor oils such as polyoxyethylene castor oil and polyoxyethylene cured castor oil (polyoxyethylene hydrogenated castor oil), polyoxyethylene beeswax derivatives such as polyoxyethylene sorbit beeswax, polyoxyethylene lanolin derivatives such as polyoxyethylene lanolin, and polyoxyethylene fatty acid amides having an HLB of 6 to 18 such as polyoxyethylene stearamide; anion surfactants, including alkyl sulfates having $C_{10}$-$C_{18}$ alkyl such as sodium cetyl sulfate, sodium lauryl sulfate, and sodium oleyl sulfate, polyoxyethylenealkylether sulfates having $C_{10}$-$C_{18}$ alkyl (with an average of 2 to 4 ethylene oxide moles added) such as sodium polyoxyethylene lauryl sulfate, and alkyl sulfosuccinates having $C_8$-$C_{18}$ alkyl such as sodium lauryl sulfosuccinate ester; and natural surfactants, including lecithin, glycerophospholipids, sphingophospholipids such as sphingomyelin, and $C_{12}$-$C_{18}$ fatty acids such as sucrose fatty acid ester. Such surfactants can be added alone or in combinations of two or more into formulations of the present invention.

The anticancer agent of the present invention may further contain a diluent, a solubilizing agent, an excipient, a pH adjustor, a soothing agent, a buffer, a sulfur-reducing agent, an antioxidant, and the like, if necessary. Examples of a sulfur-reducing agent include substances having sulfhydryl such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and $C_1$-$C_7$ thioalkane acid. In addition, examples of an antioxidant include chelating agents such as erythorbic acid, dibutylhydroxytoluene, butylhydroxyanisole, α-tocopherol, acetic acid tocopherol, L-ascorbic acid and a salt thereof, L-ascorbic acid palmitate, L-ascorbic acid stearate, sodium bisulfite, sodium sulfite, triamyl gallate, propyl gallate, ethylenediaminetetraacetic acid disodium (EDTA), pyrosodium phosphate, and metasodium phosphate. Further, the anticancer agent of the present invention may contain components that are usually added, including: inorganic salts such as sodium chloride, potassium chloride, calcium chloride, sodium phosphate, potassium phosphate, and sodium hydrogen carbonate; and organic salts such as sodium citrate, potassium citrate, and sodium acetate.

The anticancer agent of the present invention can be prepared by dissolving the ingredients described above into a buffer such as phosphate buffer. In such case, the pH is preferably 5 to 8.

In general, the anticancer agent of the present invention is administered via parenteral routes. For instance, the agent may be administered in the form of an injection (e.g., subcutaneously, intravenously, intramuscularly, or intraperitoneally) or transdermally, transmucosally, transnasally, or transpulmonarily. However, the agent can also be administered orally.

The anticancer agent of the present invention may be in the form of a liquid formulation or a freeze-dried formulation intended for dissolution and reconstitution before use. Examples of an excipient for freeze-drying that can be used include sugar alcohols or sugars such as mannitol and glucose.

The amount of an antibody that binds to mortalin 2 contained in the formulation of the present invention is determined depending upon the type of the disease to be treated, the severity of the disease, the patient's age, and the like. In general, a final concentration for administration of the antibody is 0.1 to 200 μg/ml and preferably 0.1 μg to 2 mg/ml.

As an example of the antibody that binds to mortalin 2, the K antibody provided in the present invention can be used. Production of the K antibody is described in detail in the Examples below.

(6) Method for Evaluating Anticancer Activity of a Substance

The present inventors have found that mortalin is a molecule peculiar to a cancer cell, and thus mortalin can be a target for cancer therapies. A substance neutralizing the mortalin expression and a substance preventing mortalin from intracellularly functioning can be a substance having anticancer activity. Thus, the intensity of the mortalin expression or the mortalin functions are analyzed in the presence of a test substance such that the anticancer activity of the test substance can be evaluated. In order to analyze the intensity of the mortalin expression, a known standard means for analyzing the gene expression such as Western analysis and Northern analysis can be used. Mortalin functions are analyzed by examining activities of p53, GRP94, and other mortalin-binding proteins.

Specifically, the anticancer activity of a test substance can be evaluated as described below.

In one embodiment, a mortalin protein is allowed to come into contact with a test substance such that the anticancer activity of the test substance can be evaluated based on contact strength. Such mortalin protein may be recombinantly produced or may be isolated from a cultured cell. The contact strength is determined as a indicator the amount of a test substance binding to a mortalin protein or a change in functions of a mortalin protein as a result of binding of a test substance to a mortalin protein. For instance, the amount of a test substance binding to a mortalin protein can be measured by immunoprecipitation or immunodepletion using an anti-mortalin antibody. Such method is based on a precipitation reaction of a mortalin protein with a specific antibody. Binding of a test substance to mortalin may affect a precipitation reaction caused by the antibody. Thus, such effect can be visualized based on SDS PAGE of an immune complex. In accordance with another method, a test substance is tagged with sepharose beads such that a "test substance-mortalin complex" in which a test substance binds to a mortalin protein can be directly precipitated. In such case, binding between mortalin and a test substance can be quantified on SDS PAGE gel. An example of a method for measuring the amount of MKT007 binding to mortalin in which such quantification is used is described in Wadhwa, R., Sugihara, T., Yoshida, A., Nomura, H., Reddel, R. R., Simpson, R., Maruta, H., and Kaul, S. C. (2000), Selective toxicity of MKT-077 to cancer cells is mediated by its binding to the hsp70 family protein mot-2 and reactivation of p53 function, Cancer Res 60, 6818-6821. Changes in mortalin protein functions can be evaluated based on, for example, an increased p53 activity as a result of neutralization of the functions of a mortalin protein to which a test substance has been bound or the extent of inhibition of cell growth as a result of such increase.

In another embodiment of the method for evaluating anticancer activity of a test substance, a cell overexpressing mortalin is produced by introducing a mortalin gene thereinto by a molecular biological means. Then, such cell or a cell lysate thereof is allowed to come into contact with a test substance, such that the anticancer activity can be evaluated based on contact strength. Such contact strength can be evaluated by measuring the amount of the test substance binding to mortalin with the use of the aforementioned immunoprecipitation, immunodepletion, or direct precipitation using a test substance that has been tagged with sepharose or agarose beads.

Further, in another embodiment, a cell having DNA comprising a reporter gene ligated downstream of a promoter of the mortalin gene and a cell lysate thereof are allowed to come into contact with a test substance such that anticancer activity of the test substance can be evaluated based on the expression of the reporter gene serving as an indicator. In such case, the test substance may affect in some way the mortalin promoter so that the mortalin expression level is affected. A substance causing a decrease in the mortalin expression level corresponds to a mortalin-neutralizing substance, and is likely to be an anticancer activity-having substance. DNA comprising a reporter gene ligated downstream of a promoter of the mortalin gene can be constructed as a plasmid in which a conventionally used reporter gene such as luciferase or β-gal gene is incorporated, and which is produced based on a known mortalin gene sequence in accordance with conventional methods in the field of molecular biology.

(7) Use of a Mortalin 2-Binding Substance as a Small Molecule Carrier

Since mortalin is expressed specifically on tumor cells, a substance that enters cells so as to specifically bind to mortalin can be used as a carrier for delivering small molecules into tumor cells. In addition to the anti-mortalin antibody that is internalized by live cells descried above, "mortalin 2-binding substances" such as MKT007 described in the following references can be used as a substance that specifically binds to mortalin: Wadhwa, R., Colgin, L., Yaguchi, T., Taira, K., Reddel, R. R., and Kaul, S. C. (2002), Rhodacyanine Dye MKT-077 Inhibits in Vitro Telomerase Assay But Has No Detectable Effects on Telomerase Activity in Vivo, Cancer Res 62, 4434-4438; and Wadhwa, R., Sugihara, T., Yoshida, A., Nomura, H., Reddel, R. R., Simpson, R., Maruta, H., and Kaul, S. C. (2000), Selective toxicity of MKT-077 to cancer cells is mediated by its binding to the hsp70 family protein mot-2 and reactivation of p53 function, Cancer Res 60, 6818-6821.

For instance, in order to transfer low-molecular-weight compounds, peptides, lipids, or oligonucleotides (e.g., siRNA, shRNA, miRNA, double stranded RNA, ribozyme, aptamer, and dumbbell DNA) into cells, an anti-mortalin antibody (monoclonal/polyclonal) and other substances that specifically bind to mortalin can be used.

For instance, a substance that specifically binds to mortalin is used as a drug carrier for target therapies so that immunotoxicins, peptides, nucleotides, organic molecules, and other small molecules can be transported into tumor cells.

In the internalization of a nonfluorescent substance (Qdot) or a fluorescent substance useful for visualization of cells for in vitro or in vivo live imaging of cells, an anti-mortalin antibody (monoclonal/polyclonal) or other substances that specifically bind to mortalin can be used as carriers of a contrast agent. For instance, for the purpose of examining cancer metastasis in vivo, cells are labeled with Qdots with the use of the capability of being internalized by cells (or the carrier property) of an anti-mortalin antibody, and then, the cells are injected into a nude mouse. In that case, since live images of metastasis of such cells can be observed in vivo, operations such as scarification of animals are not required.

(8) Use of an Anti-Mortalin Antibody that is Internalized by Cells

With the use of a full-length mortalin as an antigen, a polyclonal or monoclonal antibody that can be taken up into (internalized by) live cells can be produced. It is particularly preferable to use such antibody as the molecule carrier described above. The cause of the internalization of an anti-mortalin antibody has not been clearly elucidated. However, it is considered that interaction between mortalin expressed on the cell surface and interleukin 1 receptor type 1 (IL-1R type 1) is involved in such internalization to some way. Thus, internalization of the mortalin antibody is further promoted by suppression of the expression of interleukin 1 receptor type 1 or neutralization of interleukin 1 receptor type 1.

In addition, such anti-mortalin antibody (anti-mortalin 2 antibody having a capability of being internalized) is internalized specifically by cancer cells. Thus, such antibody is useful as a carrier for delivering drugs selectively to cancer cells and is also useful for cancer therapies.

Further, such anti-mortalin 2 antibody having the capability of being internalized can be used not only alone but also in combination with a means for suppression of IL-1R type 1 expression or neutralization of IL-1R type 1 (e.g., antibody, antagonist, siRNA, and ribozyme).

(9) Use of an Anti-Mortalin Antibody for Immunostaining of Cells

When cells are immunostained with an anti-mortalin antibody, staining is widely observed throughout the cytoplasm (pancytoplasmic) in normal cells. However, staining is observed in the vicinity of the nucleus (perinuclear) in cancer cells. In addition, with induction of senescence in cancer cells, shift of staining pattern from the pancytoplasmic type to perinuclear type is observed.

Focusing on such staining patterns, if an anti-mortalin monoclonal antibody derived from a hybridoma clone is used, as with the case of an anti-mortalin polyclonal antibody (K antibody), it is possible to design a kit that can detect senescent cells. That is to say, an anti-mortalin monoclonal antibody or an anti-mortalin polyclonal antibody can be used for detecting and selecting senescent or normalized cells in a cancer cell population. Specifically, such use of an anti-mortalin monoclonal antibody or an anti-mortalin polyclonal antibody involves the use of mortalin staining patterns. Transformation of cancer cells into senescent or normalized cells with a test substance can be examined by detecting or selecting senescent or normalized cells. Specifically, mortalin staining patterns can be used for screening for a test substance (e.g., low-molecular-weight compound, peptide, nucleotide, or antibody) that causes transformation of cancer cells into senescent or normalized cells.

The present invention is explained in greater detail in the Examples described below. However, the present invention is not limited to such Examples. Various modifications and changes of the present invention can be made by persons skilled in the art. Such modifications and changes are within the technical scope of the present invention.

Example 1

Mortalin Gene Expression in Tumor and a Tumor-Derived Cell Line

The mortalin gene expressions in human transformed cells, a tumor-derived cell line, and tumor tissue were analyzed by Northern and Southern blottings.

Test Method

Northern Blotting

Total RNA was prepared from normal human cells and transformed human cells using Trizol (Life Technologies, Inc). The obtained RNA was subjected to denaturing size fractionation on 1% agarose gel containing 2.2 M formaldehyde, followed by transfer to a Hybond N+ membrane (Amarsham Corp.). A probe used was a 0.5 kb of a carboxy terminal fragment of the human cDNA obtained from Hela cell-derived cDNA with the use of the mouse cDNA as a probe. Hybridization was carried out at 65° C. in Express Hybridization Buffer (CLONTECH). The membrane was washed for 10 minutes each with 2×SSC and 0.1%-SDS-containing 2×SSC, followed by washing twice with 0.1%-SDS-containing 1×SSC. The amount of RNA loading on the blot was determined using an actin probe or an 18S ribosomal probe.

Western Blotting

Protein samples (10 to 20 µg) were separated on SDS polyacrylamide gel, and then transferred to a nitrocellulose membrane (BA85, Schleicher and Schuell) by electroblotting using a semi-dry transfer blotter (Biometra, Tokyo). Immunoassay was carried out using anti-mortalin antibodies (T antibody and K antibody described below). The thus formed antibody complexes were visualized using horseradish peroxidase (HRP) or alkaline phosphatase-binding anti-mouse/rabbit immunoglobulin G (IgG) (ECL kit, Amersham pharmacia Biotech).

Results

Figure 2:
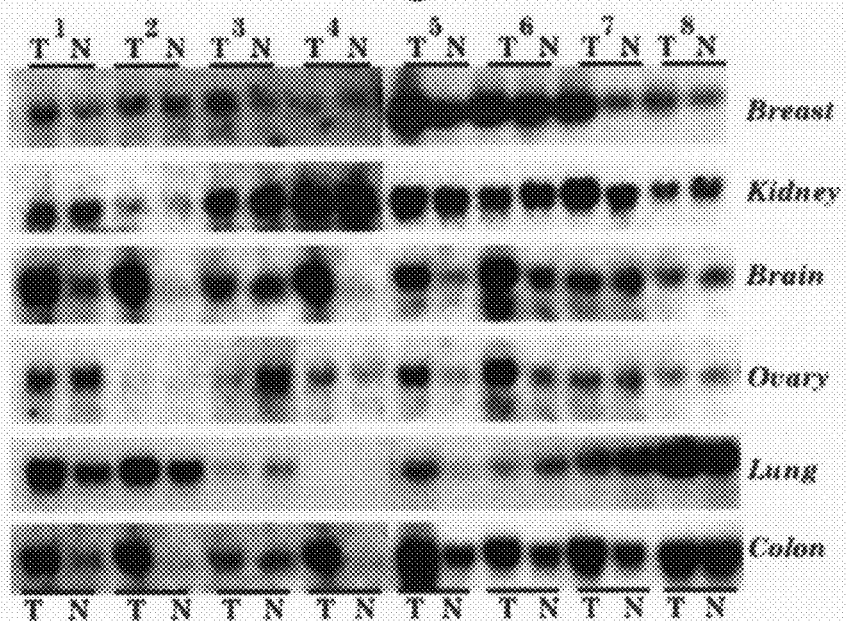
FIG. 2 shows the results of analyzing the dot blotting (each contains 2 μg of polyA RNA) for the mortalin gene expression in various types of tumor tissues (T) and the matched normal tissues (N). (Example 1)
Figure 3:
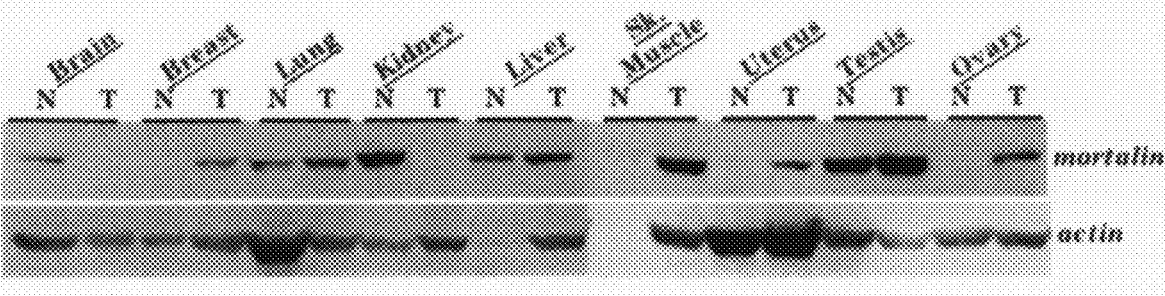
FIG. 3 shows the results of Western blotting using a mortalin-specific polyclonal antibody, which analyzes for the mortalin gene expression in various types of tumor tissues (T) and the mached normal tissues (N) as controls. As a control for the loading amount, actin was used (Example 1).

FIGS. 1 to 3 and table 1 show the results of examining mortalin gene expression in breast, brain, colon, and ovary tumor tissues and the corresponding normal tissues (controls). FIGS. 1 and 2 show dot blots indicating the expression in each tumor tissue (Tumor) and in the corresponding normal tissue (Normal). FIG. 3 shows the results of Western blotting using a polyclonal antibody specific for mortalin indicating the expression in each tumor tissue (T) and the corresponding normal tissue (N). These results are summarized in Table 1. In Table 1, columns indicate the following items, respectively, from the left: tumor types, the number of specimens, the number of specimens in which mortalin was upregulated (Mot-UP), the number of specimens in which mortalin was down-regulated (Mot-DOWN), and the number of specimens in which there was no change in mortalin expression (Mot-NO-CHANGE). Based on these results, it is found that mortalin gene expression was enhanced in almost all types of tumor tissues compared with normal tissues as controls.

TABLE 1

| Tumor type | Number of specimens | Mot-UP | Mot-DOWN | Mot-NO-CHANGE |
|---|---|---|---|---|
| Adrenal tumor | 1 | 0 | 1 | 0 |
| Breast cancer | 14 | 8 | 0 | 6 |
| Brain tumor | 10 | 6 | 1 | 3 |
| Bladder cancer | 1 | 1 | 0 | 0 |
| Colon cancer | 9 | 7 | 0 | 2 |
| Gallbladder cancer | 1 | 1 | 0 | 0 |
| Renal tumor | 10 | 1 | 1 | 8 |
| Liver cancer | 1 | 0 | 0 | 1 |
| Lymphoma | 1 | 0 | 0 | 1 |
| Lung tumor | 11 | 4 | 3 | 4 |
| Ovarian/uterus cancer | 12 | 5 | 1 | 6 |
| Pancreas cancer | 1 | 0 | 0 | 1 |
| Parotid gland cancer | 1 | 1 | 0 | 0 |
| Prostate cancer | 1 | 1 | 0 | 0 |
| Rectal cancer | 1 | 0 | 0 | 1 |
| Gastric/duodenal cancer | 2 | 1 | 0 | 1 |
| Testis cancer | 1 | 0 | 1 | 0 |
| Thymus tumor | 1 | 1 | 0 | 0 |
| Thyroid tumor | 1 | 1 | 0 | 0 |
| Ureter cancer | 1 | 0 | 0 | 1 |
| Skeletal muscle | 1 | 1 | 0 | 0 |
| Total | 82 | 39 | 8 | 35 |

Figure 4:
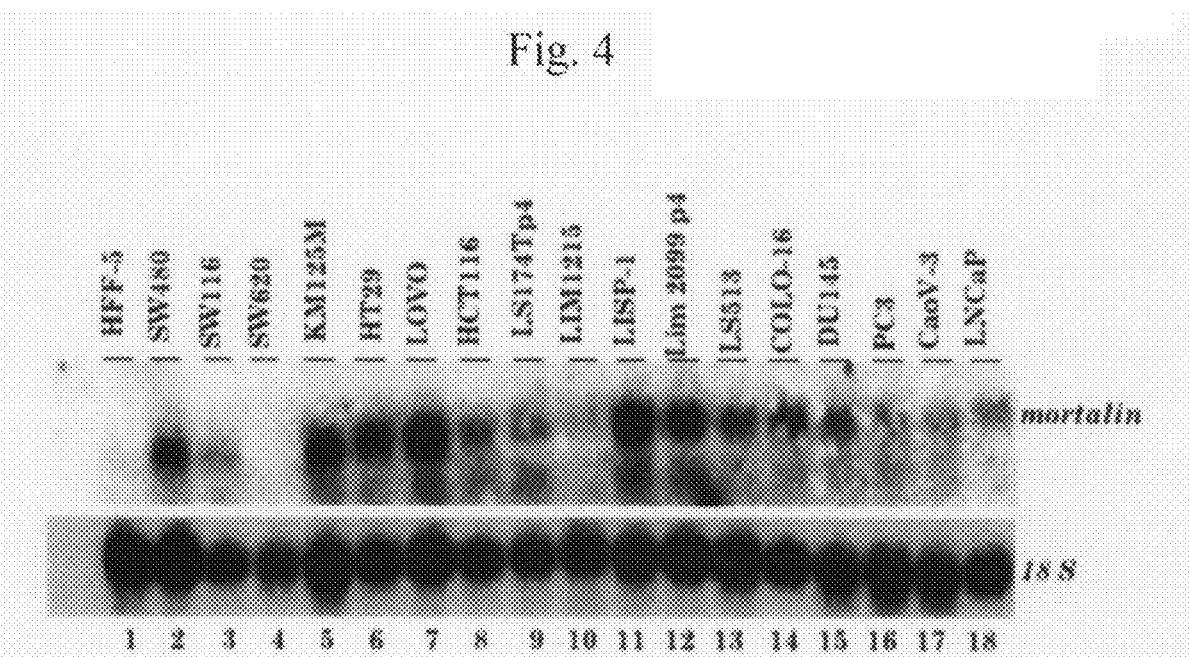
FIG. 4 shows the results of examining the mortalin expression in a normal foreskin fibroblast (HFF5: lane 1), colon cancer cells (SW480, SW116, SW620, KM125M, HT29, LOVO, HCT116, LS174Tp4, LIM1215, LISP-1, LIM2099p4, LS513, and COLO-16; lanes 2-14), and prostate cancer cells (DU145, PC3, CaoV-3, and LNCaP; lanes 15-18) (Example 1).
Figure 5:
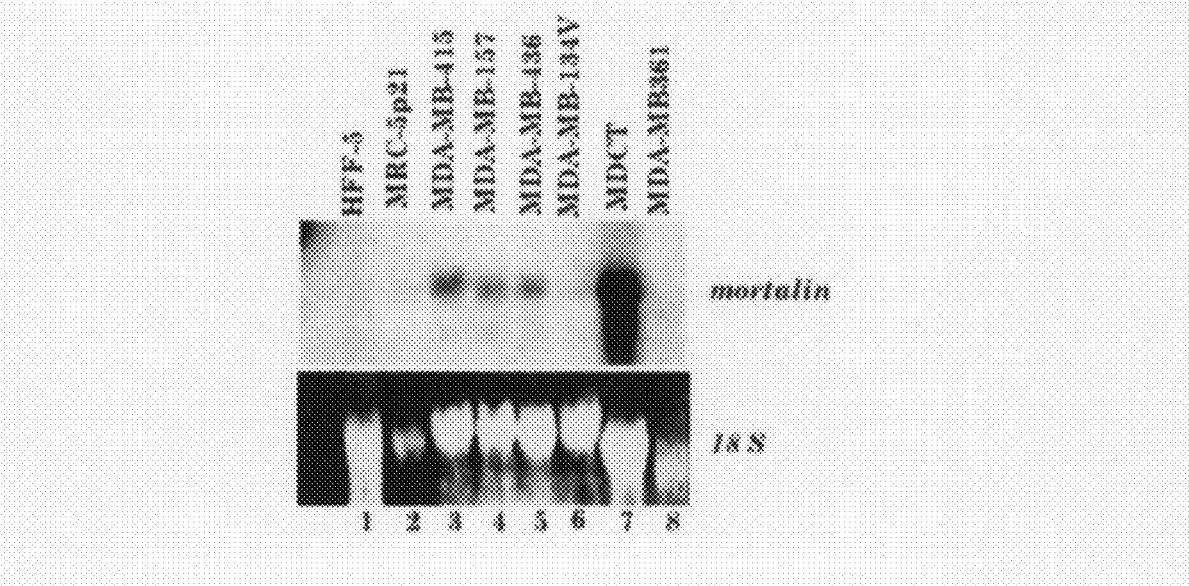
FIG. 5 shows the results of examining the mortalin expression in a normal foreskin fibroblast (HFF5: lane 1), a normal lung fibroblast (MRC5p21; lane 2), and breast cancer cells (MDA-MB-415, MDA-MB-157, MDA-MB-436, MDA-MB-134V, MDCT, and MDA-MB361; lane 3-8) (Example 1).
Figure 6:
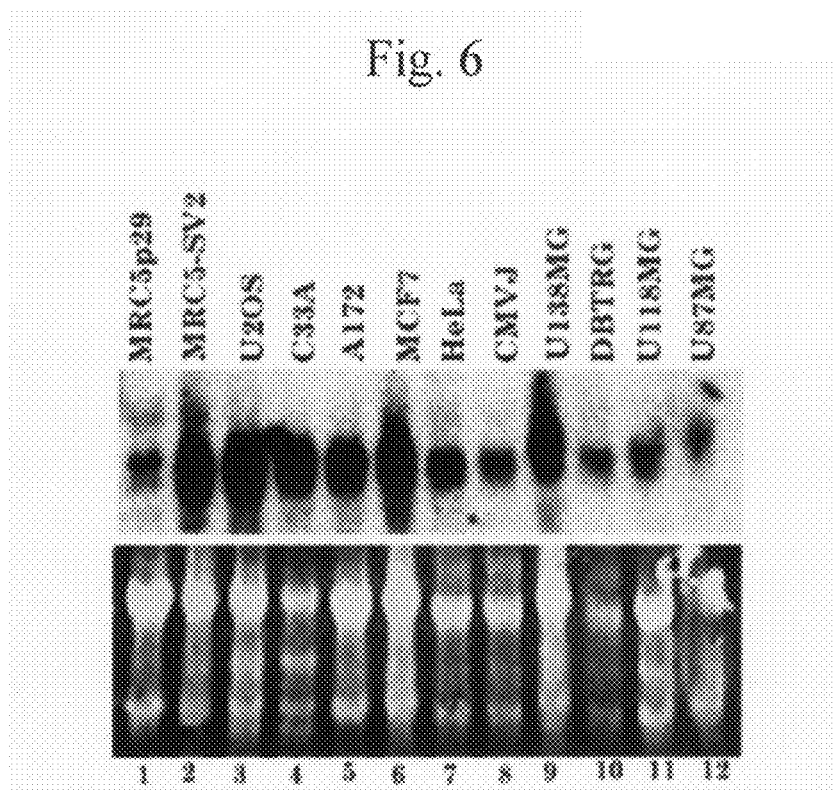
FIG. 6 shows the results of examining the mortalin expression in a normal lung fibroblast (MRC5), cells transformed with SV40 (MRC5-SV2 and U87MG), osteocarcinoma (U2OS), ovarian cancer (C33A and HeLa cells), breast cancer (MCF7), and neuroglioblastomas (A172, U138MG, DBTRG, U118MG, and U87MG) (Example 1).

Next, FIGS. 4 to 6 show the results of examining mortalin gene expression in tumor-derived cell lines. FIG. 4 shows the results of examining mortalin gene expression in a tumor cell line derived from each tissue. In the figure, lane 1 represents a normal foreskin fibroblast (HFF-5) as a control, lanes 2-14 represent colon cancer cells, and lanes 15 to 18 represent prostate cancer cells. 7 out of 13 samples of colon cancer cells exhibited very high levels of mortalin gene expression, while on the other hand, the other 6 samples exhibited moderately increased expressions compared with a normal foreskin fibroblast. Also, 3 samples of prostate cancer cells exhibited high levels of expression compared with a normal foreskin fibroblast. In FIG. 5, lane 1 represents a normal foreskin cell (HFF-5), lane 2 represents a normal lung fibroblast (MRC5), and lanes 3 to 8 represent breast cancer cells. FIG. 6 shows the mortalin expression in a normal lung fibroblast (MRC5), cells transformed with SV40 (MRC5-SV2 and U87MG), osteocarcinoma (U2OS), ovarian cancer (C33A and HeLa cells), breast cancer (MCF7), and neuroglioblastoma (A172, U138MG, DBTRG, U118MG, and U87MG). Mortalin expression was upregulated in 5 out of 7 samples of breast-cancer-derived cells, as with the case of cells derived from osteocarcinoma, ovarian cancer, and neuroglioblastoma (FIGS. 5 and 6).

Example 2

Analysis of Mortalin Expression Levels in Transformed Human Cells and Anchorage-Independent Growth Human fibroblasts were immortalized, and then cell lines exhibiting different mortalin expression levels were obtained therefrom. The cell lines were subjected to anchorage-independent colony formation assay to investigate the relationship between mortalin expression level and anchorage-independent growth potential. Anchorage-independent growth potential, that is, the cell growth ability in suspension without cell adhesion such as in soft agar, is a property common to malignantly transformed cells.

Test Method

Subcloning of Human Immortalized Cells

Figure 7:
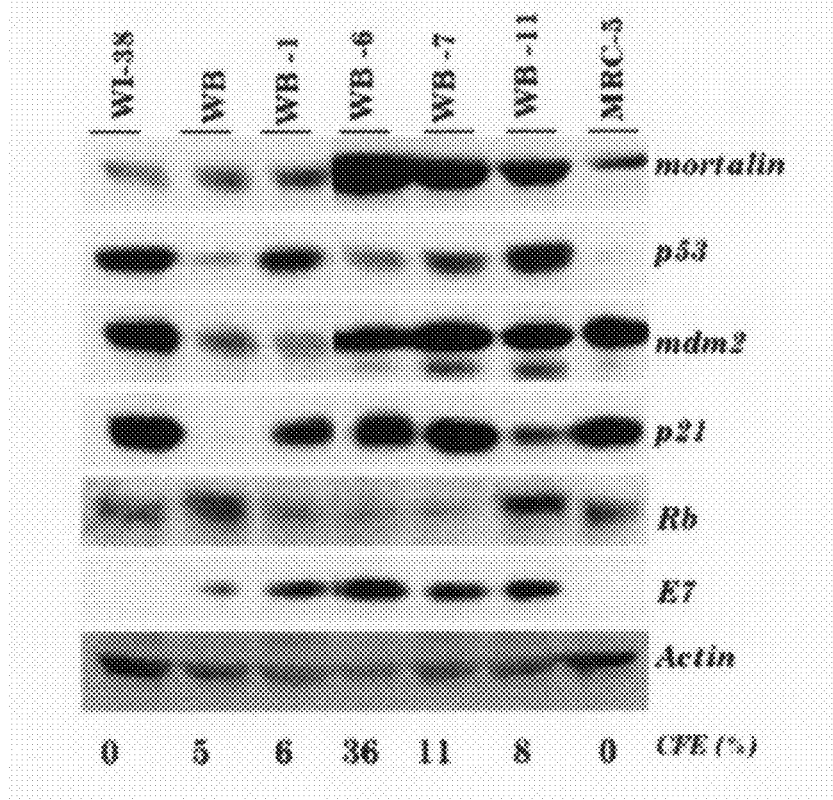
FIG. 7 shows the results of Western blotting of mortalin, p53, mdm2, p21, pRb, and E6E7 with the use of a human embryonic fibroblast (WI-38) and immortalized cells (WB-1, WB-6, WB-7, and WB-11) derived from the fibroblast. The MRC5 cell is a normal human lung fibroblast (Example 2).

Human fibroblasts (provided by the University of Texas, U.S.A.) were immortalized by introducing an expression vector that expresses a catalytic subunit of telomerase hTERT alone or a combination of hTERT, E6, and E7-expressing plasmids (the expression plasmids provided by the laboratory of Dr. Roger Reddel, Sydney, Australia), followed by serial dilution for subcloning. As a result of subcloning, cell lines exhibiting different mortalin expression levels were obtained (FIG. 7).

Colony Formation Assay

Cells were treated with trypsin, and then counted. The cells were suspended in 0.8% agar in DMEM, and seeded on an agar bed plate. The plate was incubated at 37° C. in a $CO_2$ incubator for 3 to 10 weeks.

Results

Regarding the subcloned cells from the immortalized cells, FIGS. 7 to 10 show the results of analysis of the mortalin expression level based on the Western blotting as described above and the results of anchorage-independent colony formation assay.

The results of anchorage-independent colony formation assay indicated that normal cells did not grow on soft agar, while human fibroblastoma-derived cells HT1080 formed colonies with high efficiency. FIG. 7 shows the results of Western blotting and colony formation efficiency (CFE) using a human embryonic fibroblast (WI-38), immortalized cells derived therefrom which had been transformed with hTERT, E6, and E7 (WB-1, WB-6, WB-7, and WB-11), and a normal human lung fibroblast (MRC5). The immortalized cells grew poorly on soft agar. However, subclones exhibiting a high level of the mortalin expression grew efficiently or showed a high level of colony formation efficiency (FIG. 7).

Figure 8:
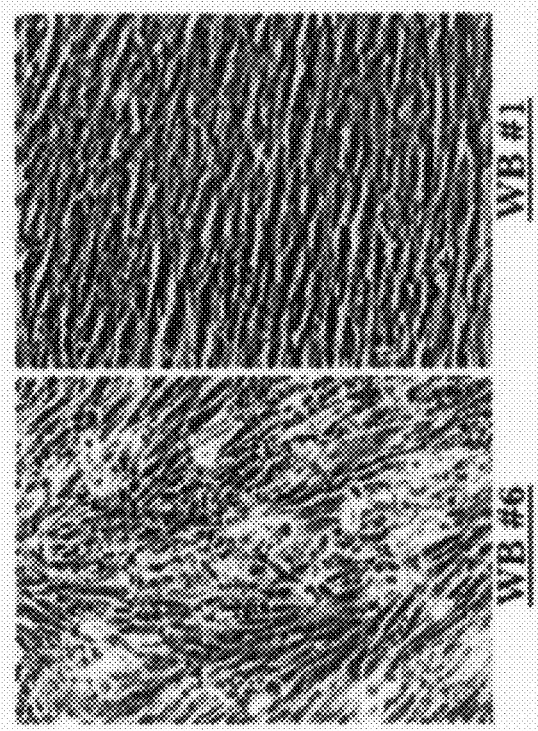
FIG. 8 shows characteristic images of the growth of WB-1 and WB-6 cells, indicating that WB-6 cells grew densely (Example 2).

FIG. 8 shows images of the growth of WB-1 and WB-6 cells in a normal medium. In particular, it is found that WB-6 grew densely. That is, these cells show the escape phenomenon from density-dependent growth inhibition, and grow densely in a normal medium.

Figure 9:
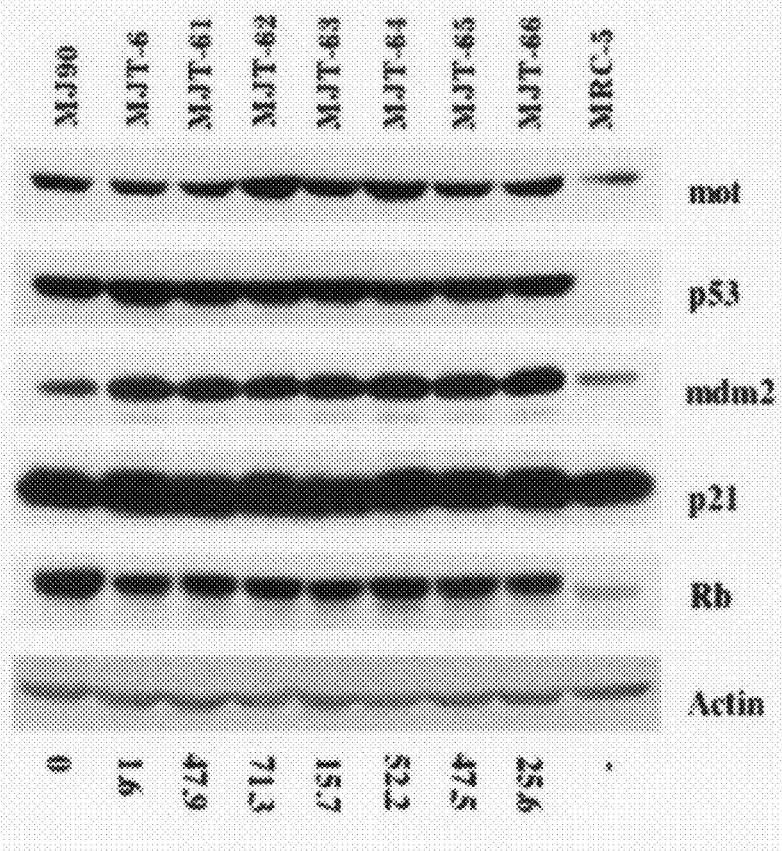
FIG. 9 shows the results of Western blotting of a normal skin fibroblast (MJ90), an immortalized cell (MJT-6) derived from the fibroblast, and various subclones thereof (MJT-61 to -66). The MRC5 cell is a normal human lung fibroblast (Example 2).

Other human immortalized cell lines were analyzed in a similar manner. FIG. 9 shows the results of Western blotting and the colony formation using a normal skin fibroblast (MJ90), a immortalized cell derived therefrom that was obtained by introducing of telomerase (MJT-6), various subclones (MJT-61 to -66) thereof, and a normal human lung fibroblast (MRC5 cell). It is shown that a high Colony Formation Rate on soft agar was achieved by subclones exhibiting high mortalin expression levels, compared with those exhibiting low mortalin expression levels. In order to exclude the possibility of crosscontamination with other transformed cells, MJ90 and MJ90-derived subclones were analyzed by DNA fingerprinting. As a result, these subclones were confirmed to be definitely derived from the corresponding cell types (FIG. 10).

Based on the results, the relationship between anchorage-independent cell growth, which is typical in tumor, and high mortalin expression levels has been revealed.

Example 3

Antibodies Specific to Mortalin

Test Method

Antibody Preparation

Rabbits (New Zealand white rabbits) were immunized with the following antigens to produce antibodies against mortalin. Five antibodies (designated as P, Q, R, S, and T antibodies, respectively) against a peptide that is a portion of murine mortalin 2 and an antibody against a full-length mortalin 2 protein (K antibody) were prepared. The antibodies were purified with an affinity column containing a mortalin protein or a peptide thereof as an antigen, and then used in the experiment described below.

1. Antigen-P: mortalin peptide $^1$Met-Ile-Ser-Ala-Ser-Arg-Ala-Ala-Ala-Ala-Arg-Leu-Val-Gly-Thr-Ala-Ala-Se r-Arg-Ser-Cys$^{20}$-OH 2. Antigen-Q: mortalin peptide $^{487}$Cys-Gln-Gly-Glu-Arg-Glu-Met-Ala-Gly-Asp-Asn-Lys$^{498}$-OH 3. Antigen-R: mortalin peptide $^{613}$Cys-Glu-Glu-Ile-Ser-Lys-Val-Arg-Ala-Leu-Leu-Ala-Arg-Lys$^{625}$-OH 4. Antigen-S: mortalin peptide $^{613}$Cys-Glu-Glu-Ile-Ser-Lys-Met-Arg-Ala-Leu-Leu-Ala-Gly-Lys$^{625}$-OH 5. Antigen-T: mortalin peptide $^{469}$Ser-Gln-Val-Phe-Ser-Thr-Ala-Ala-Asp-Gly-Gln-Thr-Gln-Val-Glu-Ile-Lys-V al Cys$^{487}$-OH 6. Antigen-K: His-tagged full-length mortalin protein (expressed in *Escherichia coli* and purified with NTA-Ni agarose)

A 2.0-kb open reading frame (ORF) of a mortalin cDNA clone obtained by screening a cDNA library with the use of an antibody against a murine-cell-derived mortalin 2 protein was cloned into a pQE30 vector (Qiagen) to obtain a His-tagged protein. This antibody used is described in detail in Wadhwa, R., Kaul, S. C., Ikawa, Y., and Sugimoto, Y. (1993) J Biol Chem 268, 6615-6621. An *Escherichia coli* cell line M15 was transformed with the pQE30/mortalin construct, allowed to grow to an $OD_{580}$ of 0.6, and induced with isopropyl-1-thio-β-D-galactopyranoside (IPTG) (0.2 mM) at 37° C. for 5 hours. The cell lysates induced with or without IPTG were analyzed by SDS-polyacrylamide gel electrophoresis, and subjected to Western blotting with an anti-His antibody (Qiagen). An anti-mortalin antibody (K antibody) that is a rabbit polyclonal antibody was prepared using the His-tagged recombinant protein.

Cellular Uptake of Antibodies

Glass cover slips were placed in a 12-well culture dish, and cells were seeded on the cover slips. After 24 hours, 5 μl of the K antibody (K-Ab; anti-mortalin antibody) obtained by immunization with the aforementioned antigen K was added to the culture solution (1.0 ml). After 12 to 24 hours, the cells were immobilized, followed by secondary staining with a fluorescein isothiocyanate-sheep anti-mouse IgG and a Texas Red-anti-rabbit IgG (Amersham Corp.) for visualization. The cells were then observed with a fluorescence microscope (Carl Zeiss). P, Q, R, S, and T antibodies were subjected to similar procedures.

Results

First, the specificity to mortalin was confirmed for five antibodies (P, Q, R, S, and T antibodies) that were raised against mortalin peptides and an antibody (K antibody) that were raised against a full-length mortalin protein. Based on Western blotting and immunoprecipitation, R, S, T, and K antibodies were confirmed to specifically react with human mortalin and murine mortalin. The K antibody detected one band having the expected size on Western blots (FIG. 11). Specific precipitation of mortalin with the K antibody was detected by immunoprecipitation (FIG. 12).

Figure 13:
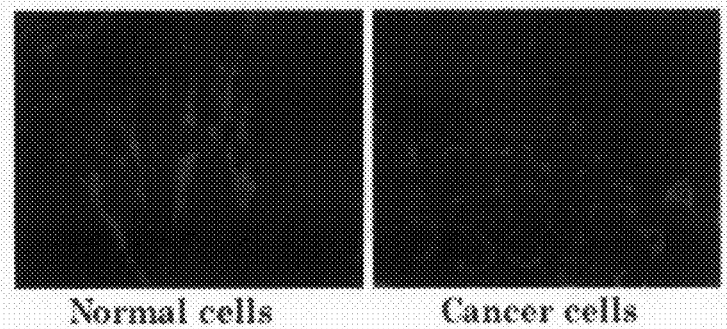
FIG. 13 shows mortalin immunostaining in normal cells (Normal cells; TIG-1) and tumor cells (Cancer cells; U2OS) with the use of the mortalin-K antibody. The cells were immobilized with methanol-acetic acid (1:1) and stained with the Mortalin-K antibody, followed by detection using a secondary fluorescent-tagged anti-rabbit antibody (rabbit Alexa 488, Molecular Probes) (Example 3).

In the cases of normal cells and transformed cells, different mortalin staining patterns were observed (FIG. 13). This result is consistent with the previous report (see Non-Patent Document 2).

Figure 14:
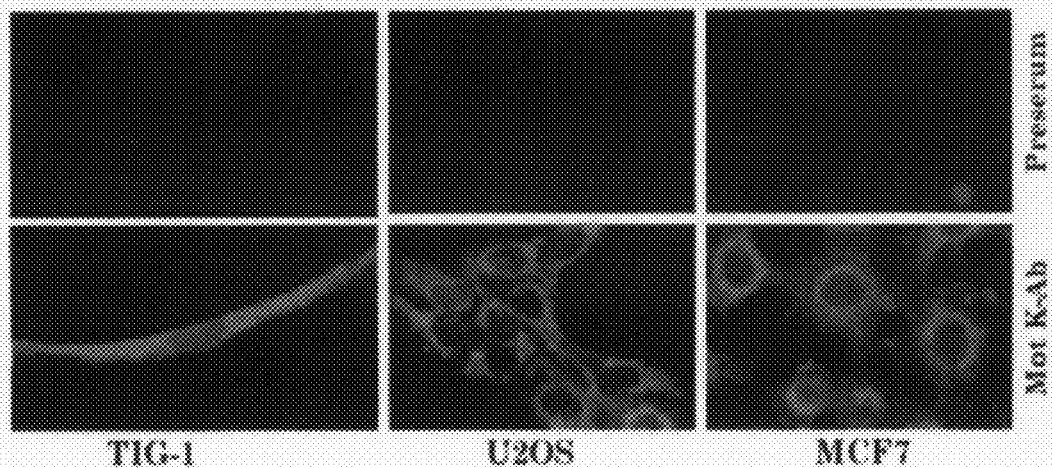
FIG. 14 shows images of internalization of the Mortalin-K antibody (mot-K Ab) in normal human cells (TIG-1) and mutant human cells (U2OS and MCF-7) (Example 3).

FIG. 14 shows very interesting results indicating that the K antibody was taken up into cells in culture by adding the antibody to a culture medium. FIG. 14 shows that the Mortalin-K antibody (mot-K Ab) was internalized by both normal (TIG-1) and mutant (U2OS and MCF-7) human cells. These staining patterns were equivalent to those obtained by immortalizing cells and staining with the K antibody (see Non- Patent Document 2). The other antibodies were also used for Western blotting and immunoprecipitation. However, such internalization was not observed.

Figure 15:
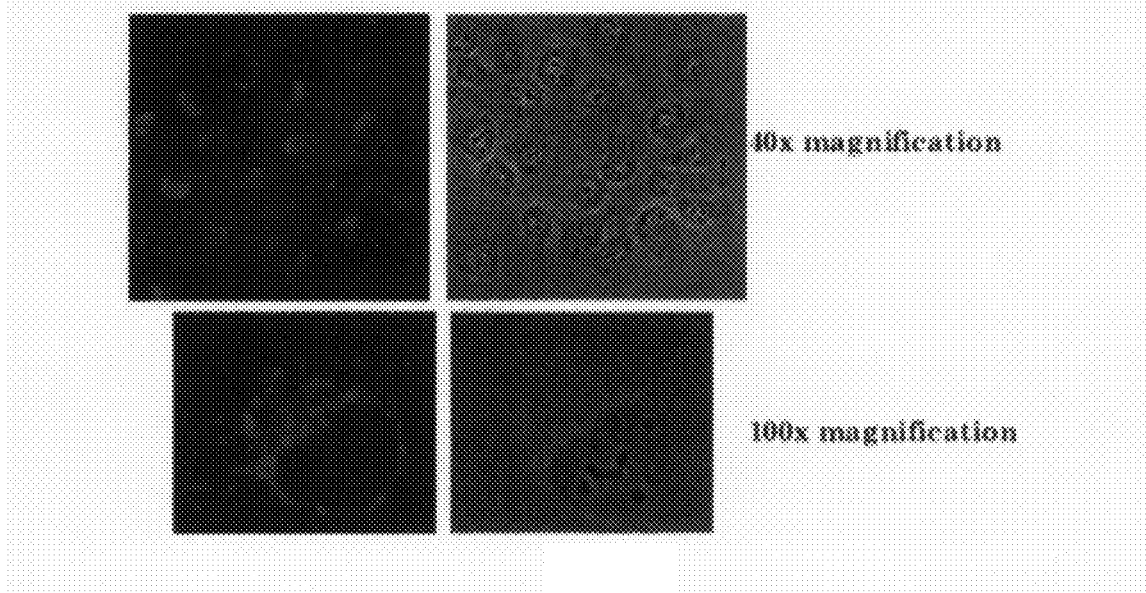
FIG. 15 shows images of mortalin staining in U2OS cells with the use of the Qdot-K antibody (Example 3).
Figure 16:
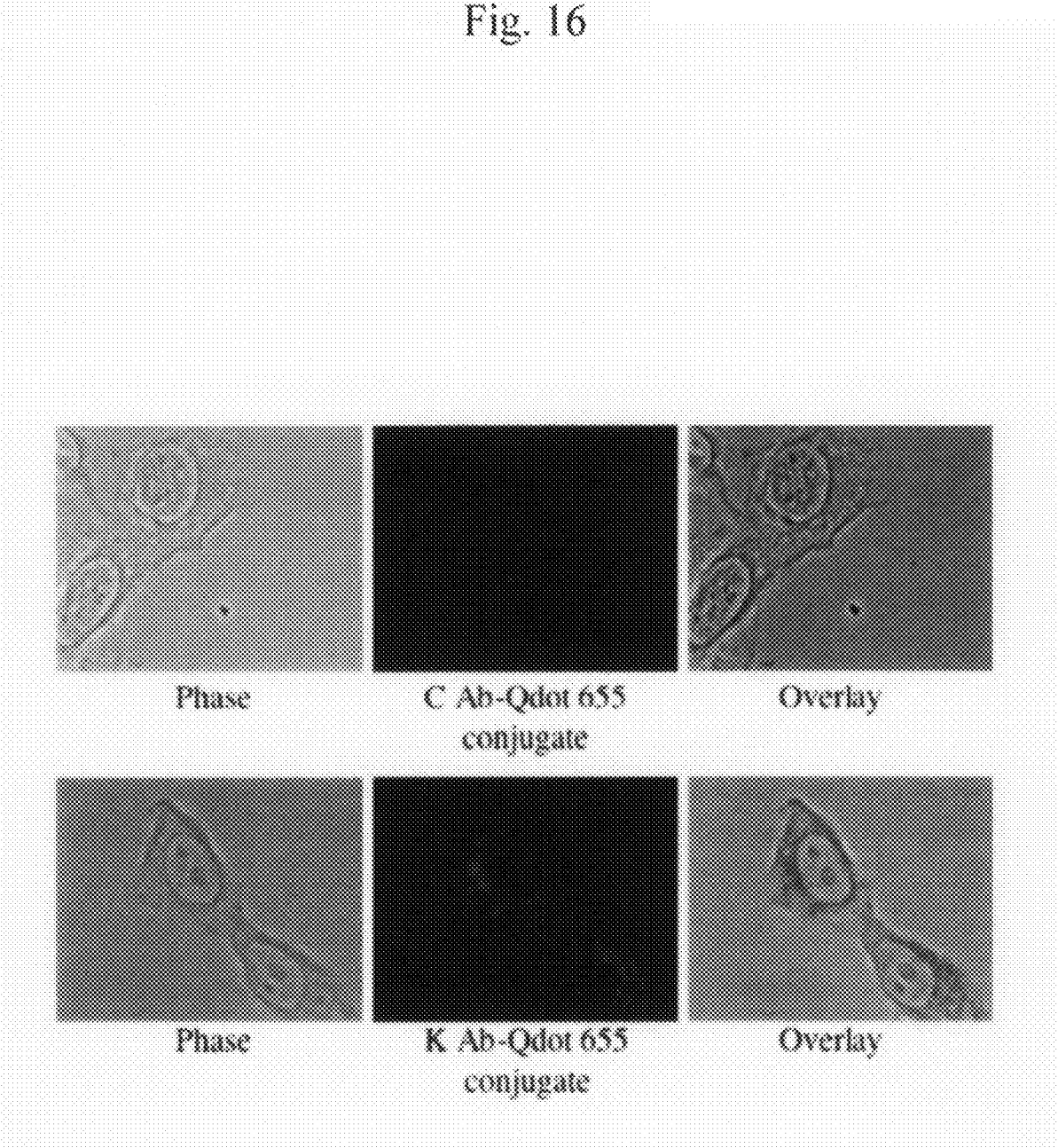
FIG. 16 shows internalization of the Qdot-K antibody (KAb-Qdot655 conjugate) by cells (lower panels). A Qdot-control antibody (CAb-Qdot655 conjugate) was not incorporated into cells (upper panels) (Example 3).

The present inventors produced a Qdot-antibody conjugate with the use of a Qdot655 antibody conjugation kit (Quantum Dot Corporation, U.S.A). When carrying out antibody staining of cells with the Qdot conjugate-K antibody, staining patterns were obtained as expected (FIG. 15). A Qdot-K antibody conjugate (approximately 5 µg/ml) was added to a culture medium containing U2OS cells. The cells were immortalized in methanol/acetone (50/50, v/v) for 10 minutes on ice. The cells were then observed using a Carl Zeiss microscope (Omega Optical, Inc.) equipped with a Qdot filter set XF 305-1 (with excitation filter 425DF45, dichroic 475DCLP, and emission filter 655DF20). As shown in FIG. 16, Qdot655 binding to a K antibody was exclusively found in the cells. This data revealed that internalization of the K antibody and Qdot binding thereto had occurred. In the cases of the other antibodies, internalization was not observed, although specific binding was observed by Western assay and immune precipitation assay.

Example 4

Use of K Antibodies for Tumor Therapies

As a result of the aforementioned experiment, it was found that mortalin is upregulated in tumor cells and that K antibodies against mortalin are internalized by cells. Next, it was examined whether or not it would be possible to affect tumor growth in some way via in vivo neutralization of mortalin in a tumor with the use of K antibodies.

Test Method

Tumor Formation in Nude Mice

Nude mice were purchased from CLEA Japan, Inc. Human fibrosarcoma cells (HT1080) were subcutaneously injected into the nude mice. When small tumor buds appeared, K antibodies (K-Ab) that is an anti-mortalin antibody were injected into a test tumor. DMEM containing preimmune serum (preserum) was injected into a control tumor. Thereafter, tumor progress was observed.

Results

Figure 17:
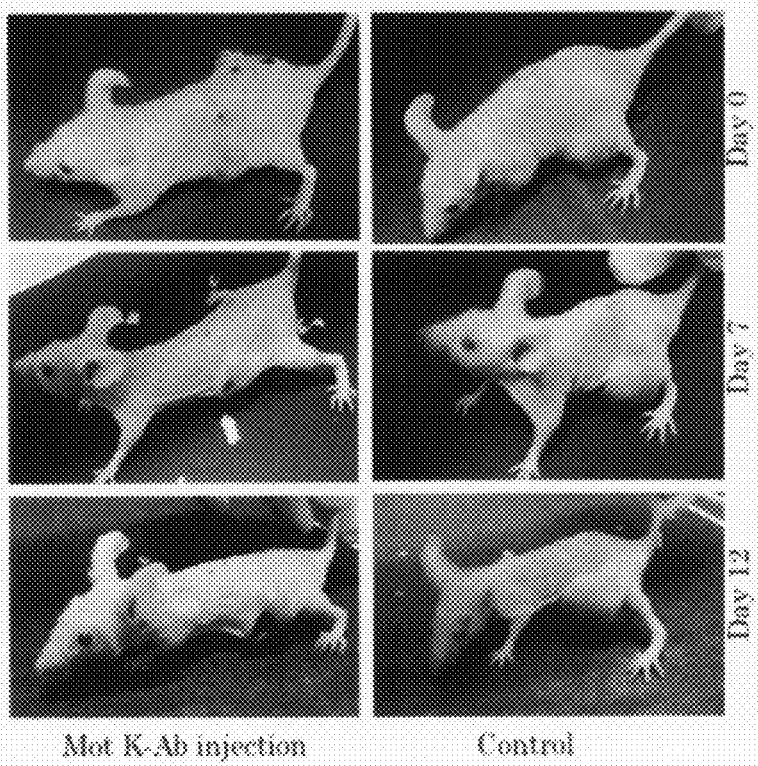
FIG. 17 shows images of the results of nude mouse assay using HT1080 cells obtained after the injection of the Mortalin-K antibody (Mot K-Ab injection). The Mortalin-K antibody and the control antibody were injected into the formed tumor buds (approximately 6 mm), and the progress of tumors was observed (Example 4).
Figure 18:
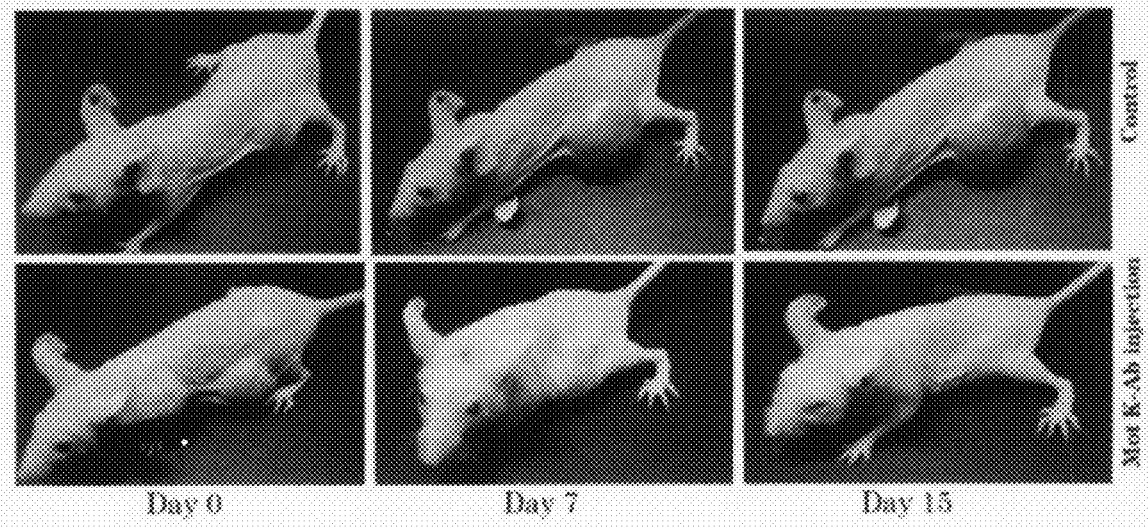
FIG. 18 shows images of the results of nude mouse assay using HT1080 cells after injection of the Mortalin-K antibody (Mot K-Ab injection). When tumor buds (approximately 6-8 mm) were formed, the control antibody and the mortalin-K antibody were separately injected thereinto, followed by observation of the resulting progress (Example 4).

In Experiment 1, 5 days after injection of HT1080 cells ($1 \times 10^6$ cells), small tumor buds appeared. The tumors were injected with mortalin K antibodies (Mot-K Ab) or preserum (Control) (5 µl in 500 µl of DMEM). The tumor into which the antibodies had not been injected grew to not less than 2 cm in size in 12 to 15 days. However, the tumor into which the antibodies had been injected grew to only 1 cm in size for 4 weeks (FIGS. 17 and 18).

Figure 19:
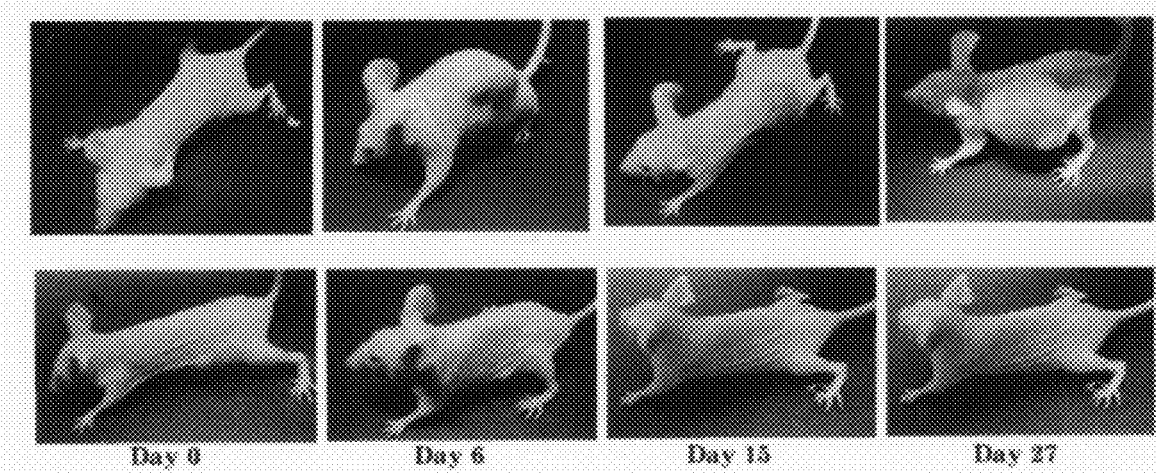
FIG. 19 shows images of the results of nude mouse assay using HT1080 cells after injection of the Mortalin-K antibody (Mot K-Ab injection). The mortalin-K antibody was injected into a tumor (Example 4).

In Experiment 2, HT1080 cells ($1 \times 10^5$ cells) were injected into mice, and then the injection of antibodies was initiated when the sizes of tumor buds became approximately 1 to 2 mm. During one month thereafter, the progress of tumor growth was observed while the injection was repeated every 5 days. The size of the tumor into which control antibodies had been injected gradually increased. However, the tumor into which Mot-K antibodies had been injected shrank (FIG. 19).

Figure 20:
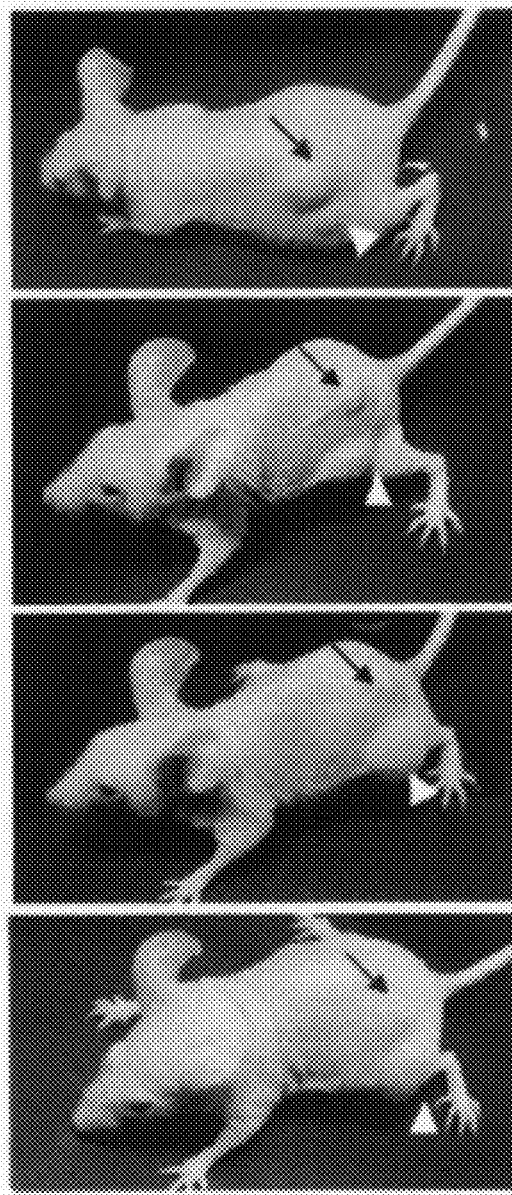
FIG. 20 shows images of the results of nude mouse assay using HT1080 cells after injection of the Mortalin-K antibody (Mot K-Ab). The mortalin-K antibody was injected into the upper tumor (Example 4).

In Experiment 3, a mouse having two tumors that were located next to each other (a large upper tumor and a small lower tumor) was used. K antibodies were injected into the upper tumor. It should be remarked that the size of the upper tumor into which K antibodies had been injected decreased, while on the other hand, the size of the lower tumor increased after 4 weeks (FIG. 20).

Example 5

K Antibody

Another lots of K antibodies (polyclonal antibodies against Mot-2 full-length protein) were prepared. It was confirmed that all lots of the antibodies could be taken up into cells.

K antibodies at three different concentrations (A-C), preserum, an affinity purified K antibody (AP), and a T-antibody as a control (antibody against a partial peptide of mortalin: $^{469}$Ser-Gln-Val-Phe-Ser-Thr-Ala-Ala-Asp-Gly-Gln-Thr-Gln-Val-Glu-Ile-Lys-Val-Cys$^{487}$-OH) were added to a culture of A549 cells (lung cancer cells), followed by culturing for 24 hours. A cell lysate was prepared from cells that had been recovered after trypsin treatment of cultured cells. Intracellularly internalized antibodies were detected by Western blotting using HRP-binding anti-rabbit antibodies. Mortalin and actin were used as internal controls so that the loading amounts of samples into each lane were adjusted to become equal.

Results

FIG. 21 shows the detection for internalized K antibodies by Western blotting. The K antibodies and the affinity purified K antibody were intracellularly internalized. However, preserum and the T-antibody were not intracellularly internalized.

Example 6

Suppression of Interleukin-1 Receptor Type 1 Expression

It has been reported that mortalin also exists on the surfaces of cancer cells (Shin, B. K., Wang, H., Yim, A. M., Le Naour, F., Brichory, F., Jang, J. H., Zhao, R., Puravs, E., Tra, J., Michael, C. W., Misek, D. E., and Hanash, S. M. (2003) J Biol Chem 278, 7607-7616; and Dundas, S. R., Lawrie, L. C., Rooney, P. H., and Murray, G. I. (2005) J Pathol).

In addition, it has been known that mortalin interacts with interleukin-1 receptor type 1 (hereafter to be also referred to as IL-1R type 1) (Sacht, G., Brigelius-Flohe, R., Kiess, M., Sztajer, H., and Flohe, L. (1999) Biofactors 9, 49-60).

The inventors of the present invention predicted that an internalization phenomenon in which K antibodies are taken up into cells would be associated with the expression of mortalin on the cell surfaces and the binding of the mortalin to IL-1R type 1.

In order to examine such prediction, an shRNA-expressing plasmid which suppresses the expression of IL-1R type 1 was constructed. Two types of shRNA-expressing plasmids were constructed, which are directed to two target sites on the cDNA (289-307 and 293-311), respectively. The sequences of the shRNA are shown in FIG. 22.

The sequences of the shRNA that are intracellularly expressed from the plasmids (2 types) constructed in the present invention are as follows:

```
5'-ACAAGUCUCUAGGAUUCAUGUGUGCUGUCCAUGAAUCCUGGAGGC
UUGUU-3';
and

5'-GCUUUCAGGAUUCAUCAACGUGUGCUGUCCGUUGAUGAAUCCUGG
AGGCUU-3'.
```

Each expression plasmid was transfected into cells, followed by analysis of the suppression of the expression of IL-1R type 1 by Western blotting using an anti-IL-1R type 1 antibody.

Results

The expression of IL-1R type 1 was suppressed with the use of each of the 2 types of shRNA-expressing plasmids shown in FIG. 22 (FIG. 22: gel image)

Promoted Internalization of K Antibody Due to the Suppression of the Expression of Interleukin-1 Receptor Type 1

Each of the 2 types of shRNA-expressing plasmids effectively suppressed the expression of IL-1R type 1 (FIG. 22: gel image). Thus, cells (HepG2) into which a control plasmid or either one of the 2 types of shRNA-expressing plasmids in FIG. 22 had been transfected were cultured with K antibodies. Then, intracellularly internalized antibodies were analyzed by Western blotting using HRP-binding anti-rabbit antibodies.

Results

Figure 23:
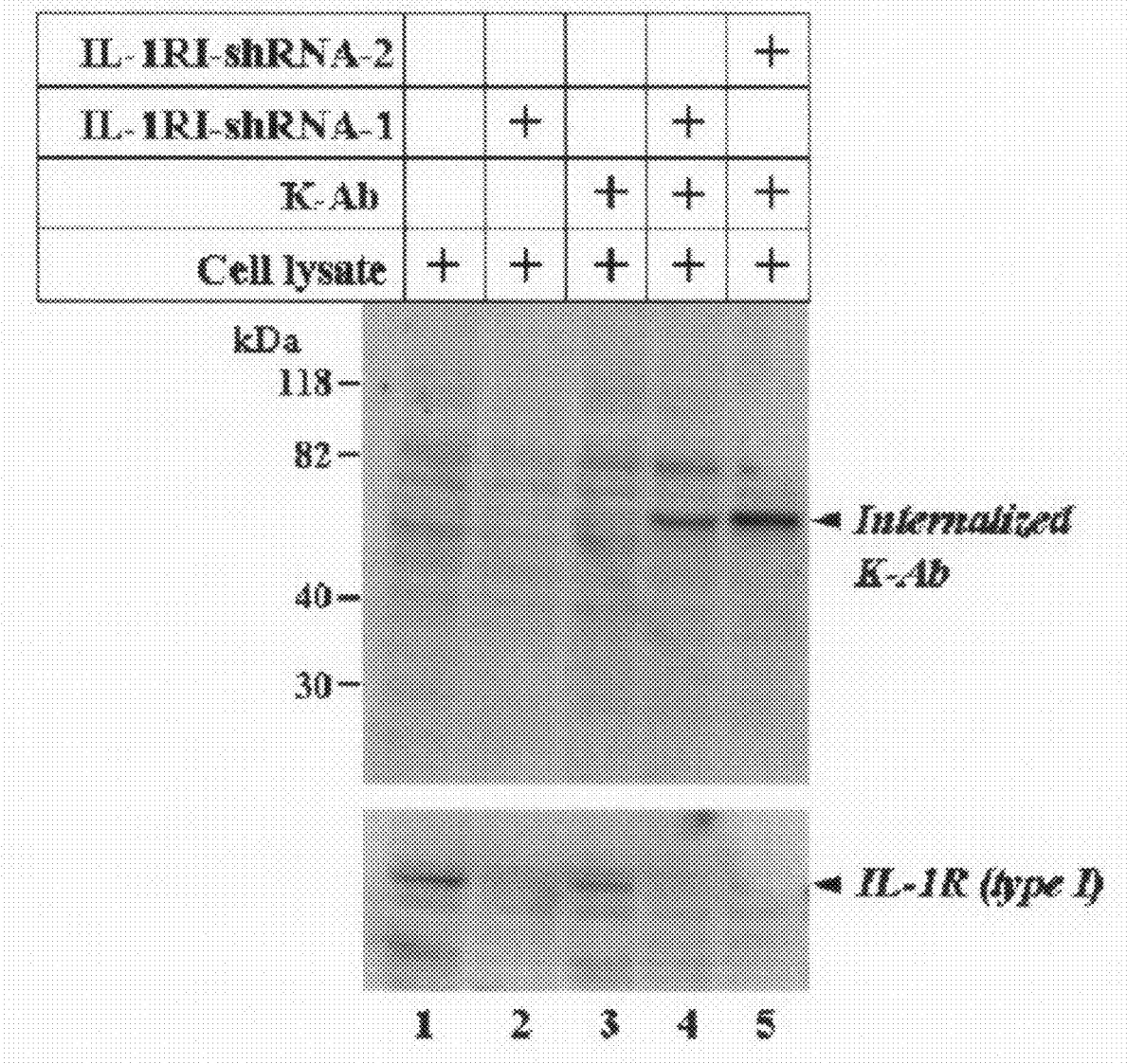
FIG. 23 shows that internalization of the K antibody by cells is promoted by the suppression of the expression of interleukin-1 receptor type 1 (IL-1R type 1) by shRNA (Example 6).

The 2 types of shRNA-expressing plasmids effectively suppressed the expression of IL-1R type 1 (FIG. 23: lower image). Meanwhile, the internalization of K antibodies by cells was promoted (FIG. 23: upper image). The experimental results support that IL-1R type 1 prevents the internalization of K antibodies and the intracellular internalization of K antibodies is promoted due to the suppression of the expression of IL-1R type 1. It is considered that binding between mortalin and IL-1R type 1 on the cell surfaces prevents the internalization of mortalin-K antibody (anti-mortalin antibody) complex by cells.

Such effect of promoting intracellular internalization is considered to be more preferably exhibited when a K antibody is used as a carrier for drug delivery or as an anticancer component. The effect of promoting intracellular internalization may be generated by the knockdown with the use of antisense nucleotide, siRNA, shRNA, miRNA, double stranded RNA, or ribozyme as well as hairpin-type RNA of interleukin-1 receptor type 1 shown in FIG. 23; or the neutralization with an antibody or an antagonist; or the expression suppression or neutralization of IL-1R type 1 by any method. Such effects are considered to promote the uptake of mortalin antibodies by cells, as shown in the data of FIG. 23.

Example 7

Monoclonal Antibodies Having 3 Properties of K Antibody

Mouse monoclonal antibodies against recombinant human full-length mortalin were prepared. I was examined whether or not the obtained 50 clones of the anti-mortalin monoclonal antibodies would meet the following three criteria of:

(1) having reactivity and specificity to mortalin as determined by Western blotting analysis;

(2) resulting in patterns of mortalin immunostaining in normal cells and cancer cells (a pattern of staining throughout the cytoplasm in normal cells and a pattern of staining of the vicinity of the nuclear envelope in cancer cells); and (3) being capable of being internalized by cells.

Results

FIG. 24 represents production of new monoclonal antibodies against mortalin and selection of anti-mortalin monoclonal antibodies having a capability of being internalized. Clones of monoclonal antibodies meeting the above 3 criteria were obtained, and were 4 out of the obtained 50 clones. Many clones that met the criteria regarding reactivity specificity and an immunostaining pattern were not internalized by cells. Finally, cells producing anti-mortalin monoclonal antibodies having a capability of being internalized (hybridomas; Nos. 37, 38, 71, and 96) were obtained. In addition, a hybridoma was prepared, as a negative control, which is a clone (No. 52) not internalized by cells but meeting the criteria regarding reactivity specificity and an immunostaining pattern.

A clone producing an anti-mortalin 2 monoclonal antibody with the highest efficiency of internalization by cells (clone 37-6) has been deposited under the terms of the Budapest Treaty of the International Recognition of the Deposit of Microorganisms for the Purposes of Patent Procedure with the International Patent Organism Depositary, National Institute of Advanced Industrial Science and Technology (AIST), Tsukuba Central 6, 1-1, Higashi 1-chome, Tsukuba-shi, Ibaraki-ken, Japan, on Aug. 23, 2005, with (Accession No.: FERM BP-10408.

Confirmation of the Intracellular Internalization of a Monoclonal Antibody

Cells were cultured with anti-mortalin monoclonal antibodies shown in FIG. 25, followed by immobilization of the cells at 24 hours thereafter and immunostaining with an FITC-binding secondary antibody.

Anti-mortalin monoclonal antibodies (37-1, 37-6, 38-4, 71-1, and 96-5) were obviously intracellularly internalized. Clone 52-3, an anti-mortalin monoclonal antibody, was not internalized.

Further, the cells were subjected to acid-washing treatment, and then the internalization of anti-mortalin monoclonal antibodies by cells were confirmed (FIG. 26). Cancer cells (U2OS) were cultured with the antibody clones shown in FIG. 26, immobilized, and then subjected to immunostaining with an FITC-binding secondary antibody for the internalized antibodies for detection. In order to avoid nonspecific detection of antibodies that adhered to the cell surfaces, the cells were washed with cooled PBS containing 0.2 M acetic acid-0.5 M NaCl prior to immobilization. The results of comparison of immunostaining intensities between cells subjected to an acid-washing treatment and cells subjected to a normal PBS washing treatment are summarized in FIG. 26.

Cells subjected to acid washing were found to remain stained without change. This fact supports that such immunostaining was definitely caused by antibodies that had been internalized by the cells. That is, it is indicated that such staining was not caused by antibodies that existed in a nonspecific state on the cell surfaces.

Example 8

Promotion of Cancer Cell-Specific Intracellular Internalization of Anti-Mortalin Monoclonal Antibodies Cancer cells (U2OS) or normal cells (TIG-1) were cultured with anti-mortalin monoclonal antibodies and anti-IL-1R type 1 antibodies. The cells were cultured for 30 minutes with the combinations of antibodies shown in FIG. 27, followed by immobilization. The anti-mortalin monoclonal antibodies that had been internalized were detected with FITC-binding anti-mouse secondary antibodies.

Results

The anti-mortalin monoclonal antibodies (37-1, 37-6, 38-4, 71-1, and 96-5) were selectively internalized by cancer cells. When clones 37-1, 37-6, and 38-4 were cultured with the anti-IL-1R type 1 antibody (Monoclonal Anti-human IL-1R type 1 Antibody, R&D Systems Inc., Catalog Number: MAB269), promotion of internalization by cancer cells was observed. In the normal cells, internalization of each clone was not promoted. In fact, the extent of internalization decreased.

Promotion of Cancer Cell-Specific Intracellular Internalization of an Anti-Mortalin Monoclonal Antibody in the Presence of an Anti-IL-1R Type 1 Antibody Cancer cells (U2OS) or normal cells (TIG-1) were cultured in the presence of an anti-mortalin monoclonal antibody (clone 37-1, 37-6, or 38-4) and an anti-IL-1R type 1 antibody, followed by immobilization at 24 hours thereafter. Anti-mortalin monoclonal antibody was then detected with an FITC-binding anti-mouse antibody.

Results

Figures 28, 29:
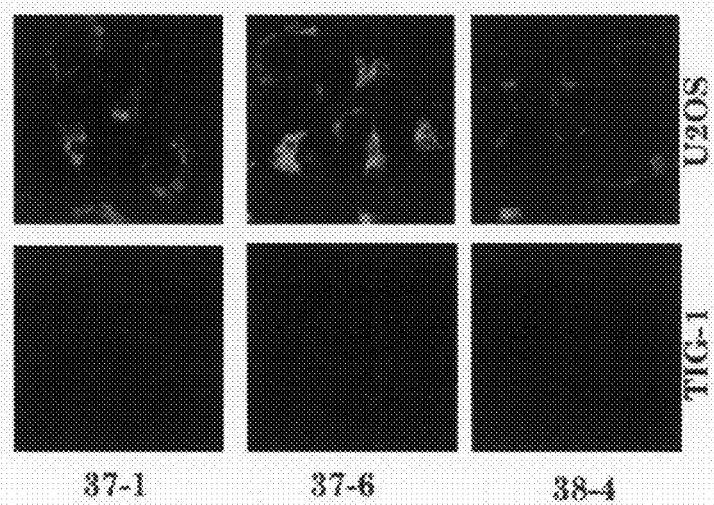
FIG. 28 shows that internalization of the anti-mortalin monoclonal antibodies (clone 37-1, 37-6, and 38-4) by cancer cells is promoted with the use of an anti-IL-1R type 1 antibody (Example 8).
FIG. 29 shows that the suppression of IL-1R type 1 expression in cancer cells (HepG2) results in selective promotion of internalization of the anti-mortalin monoclonal antibodies by the cancer cells (Example 8).

FIG. 28 shows that the anti-IL-1R type 1 antibody promoted the internalization of anti-mortalin monoclonal antibodies (clones 37-1, 37-6, and 38-4) by cancer cells.

In cancer cells, intracellular internalization of each of the 3 anti-mortalin monoclonal antibodies was observed. However, in normal cells, intracellular internalization was not observed.

Promotion of Cancer Cell-Specific Intracellular Internalization of Anti-Mortalin Monoclonal Antibodies Due to the Neutralization of IL-1R Type 1 and the Suppression of the Expression of IL-1R Type 1

FIG. 29 shows that internalization of anti-mortalin monoclonal antibodies by cancer cells was selectively promoted when the expression of IL-1R type 1 is suppressed in the cancer cells (HepG2). In cancer cells (HepG2) with high expression levels of IL-1R, knockdown of the expression of IL-1R type 1 was carried out with the shRNA-expressing plasmid. The thus transfected cells were cultured in the presence of combinations of anti-mortalin monoclonal antibodies and anti-IL-1R type 1 antibodies as shown in FIG. 29. After immobilization of the cells, the cells were visualized using an FITC-binding mouse secondary antibody.

Results

The intracellular internalization of anti-mortalin monoclonal antibodies by cancer cells was promoted by the suppression of the expression of IL-1R type 1 with shRNA and the neutralization of the receptors with IL-1R type 1-specific antibodies. shRNA acting against IL-1R type 1 or neutralizing antibodies specific for IL-1R type 1 did not affect the internalization of anti-mortalin monoclonal antibodies by normal cells.

Example 9

Relationship Between Mortalin Overexpression in Cancer Cells and Proliferation/Metastasis of Cancer Cells: Part 1

Figure 30:
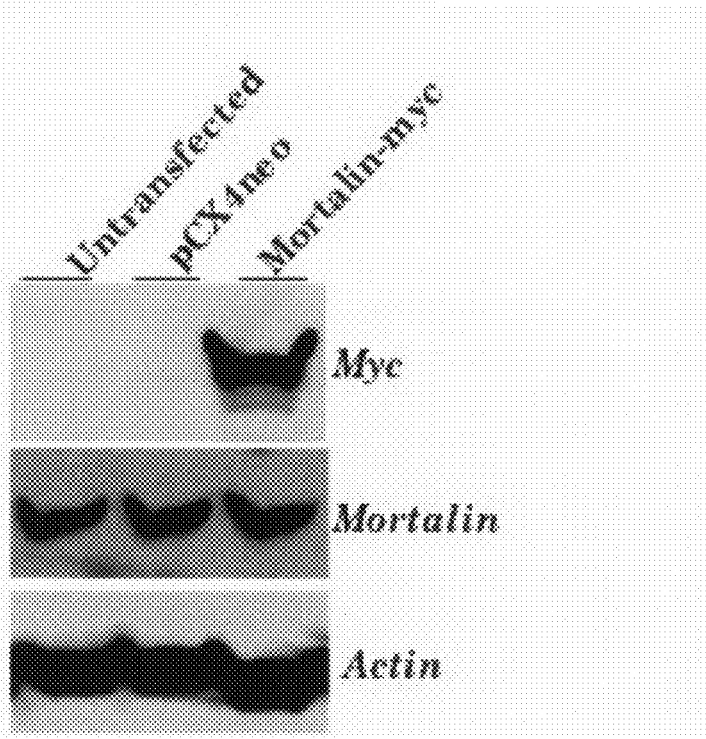
FIG. 30 shows the results of analysis of the relationship between mortalin overexpression and proliferation/metastasis in cancer cells (Part 1) (Example 9).

First, a cancer cell line used for mortalin overexpression was provided. Mortalin was overexpressed in breast cancer cells (MCF7), which do not form tumors in nude mice, with the use of a retrovirus-expressing vector. The overexpression of myc-tagged mortalin was detected by Western blotting using an anti-myc antibody (FIG. 30). The amount of protein to be run was adjusted using endogenous mortalin and actin as internal controls.

Relationship Between Mortalin Overexpression in Cancer Cells and Proliferation/Metastasis of Cancer Cells: Part 2

Figure 31:
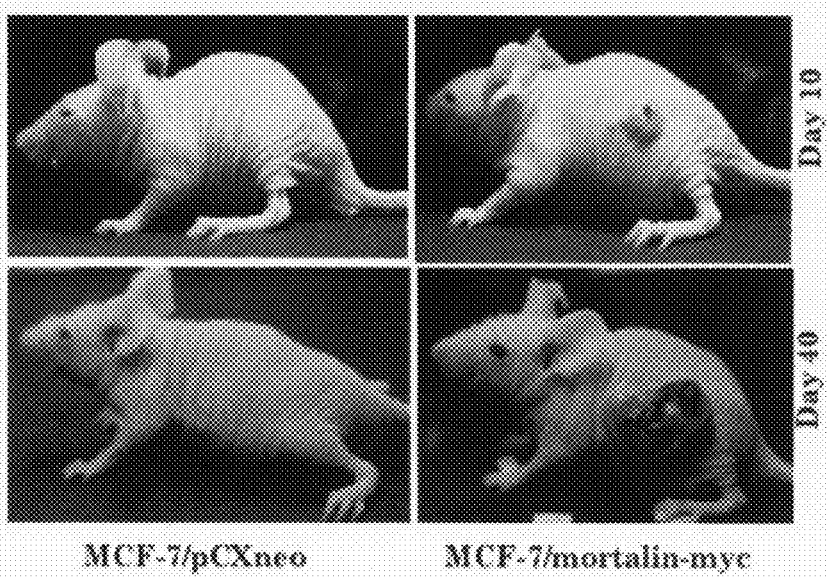
FIG. 31 shows the results of analysis of the relationship between mortalin overexpression and proliferation/metastasis in cancer cells (Part 2) (Example 9).

Next, the effect of the mortalin overexpression on the growth of malignant tumors was investigated. As shown in FIG. 31, it was examined whether or not the mortalin-constantly overexpressing breast cancer cells (MCF7), which were allowed to overexpress mortalin with the use of a retrovirus-expressing vector, would form a tumor in a nude mouse.

Results

The breast cancer cells (MCF7) overexpressing mortalin formed a tumor in a nude mouse. However, original breast cancer cells not overexpressing mortalin did not form a tumor in a nude mouse.

Accordingly, mortalin overexpression results in the growth of malignant tumors. That is, mortalin is considered to be an appropriate target for cancer therapies.

Relationship Between Mortalin Overexpression in Cancer Cells and Proliferation/Metastasis of Cancer Cells: Part 3

Figure 32:
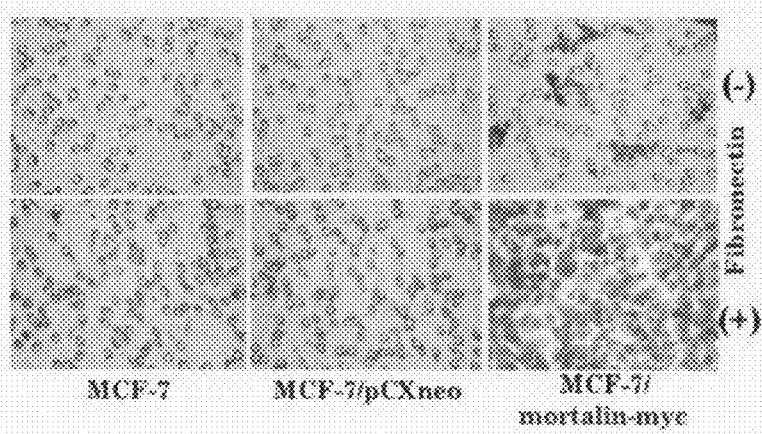
FIG. 32 shows the results of analysis of the relationship between mortalin overexpression and proliferation/metastasis in cancer cells (Part 3) (Example 9).

In FIG. 32, the relationship between mortalin overexpression and metastasis in cancer cells was analyzed. MCF7 cells were allowed to overexpress mortalin with the use of a retrovirus-expressing vector. Then, the cells constantly overexpressing mortalin were examined in terms of chemotaxis. The chemotaxis test provides a reliable indicator of cancer cell metastasis.

Chemotaxis assay was carried out in experimental control cells and mortalin-overexpressing MCF7 cells. 60% to 70% confluent cells were washed with cooled PBS, followed by trypsin treatment. Then, the resulting cells were resuspended in DMEM containing 0.5% FBS (Sigma) at a cell density of $2 \times 10^5$ cells/ml. The cells were seeded within Transwell chambers (pore size: 12 mm, Costar) at $2 \times 10^4$ cells/ml, followed by invasion assay according to the manufacturer's instruction. Human plasma-derived fibronectin (Sigma) was used as a chemoattractant.

Results

Chemotaxis was observed in the MCF7 cells overexpressing mortalin. However, chemotaxis was not observed in the original MCF7 cells.

Mortalin overexpression provides cancer cells with the ability to metastasize. That is, mortalin is considered to an appropriate target for therapies for cancer metastasis.

Relationship Between Mortalin Overexpression in Cancer Cells and Proliferation/Metastasis of Cancer Cells: Part 4

Figure 33:
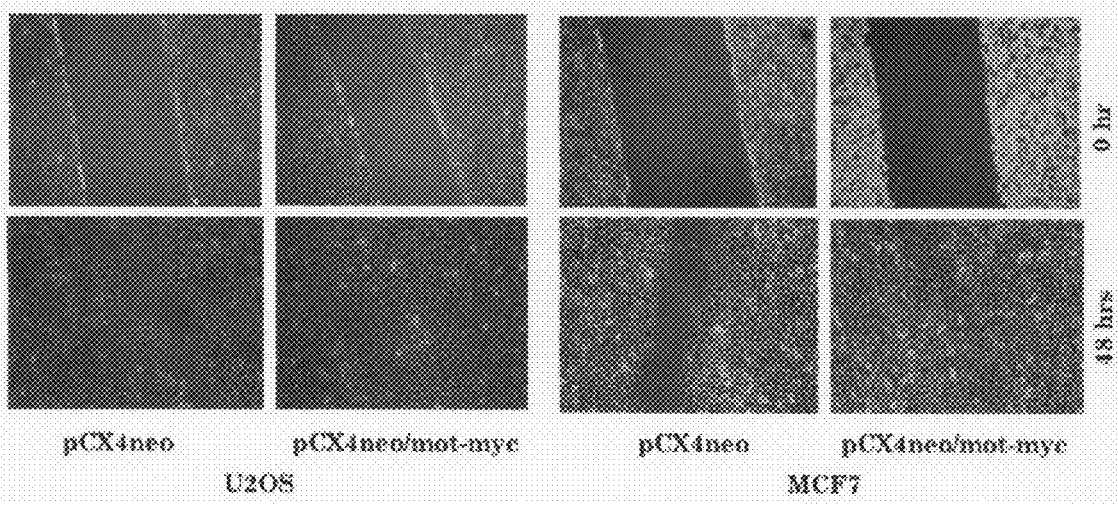
FIG. 33 shows the results of analysis of the relationship between mortalin overexpression in cancer cells and proliferation/metastasis of cancer cells (Part 4) (Example 9).

In FIG. 33, the relationship between mortalin overexpression in cancer cells and proliferation/metastasis of cancer cells was further examined. MCF7 cells were allowed to overexpress mortalin with the use of a retrovirus-expressing vector. Then, cells constantly overexpressing mortalin were examined in terms of cell mobility by scratch wound assay. The scratch wound assay can be a reliable indicator of cancer cell metastasis. Cells were monolayer-cultured on a dish, the surface of which had been coated with fibronectin (10 µg/ml). Lines were drawn on the monolayer-cultured cells using a P-200 pipet chip so as to completely recover the cells, resulting in the formation of wounds. In order to remove cell residues, the cells were washed with PBS several times. A medium was added thereto. The time when scratch wounds were made was determined as "0." During subsequent 48 hours, the cells were grown and migrated to the wounds.

Migration of the cells to the wounds was observed using an object lens (×10) of a phase-contrast microscope for recording.

Results

MCF7 and U2OS cells overexpressing mortalin exhibited a high level of mobility in scratch wound assay. Mortalin overexpression provides cancer cells with the ability to metastasize. That is, mortalin is considered to be an appropriate target for therapies for cancer metastasis.

Example 10

Figure 34:
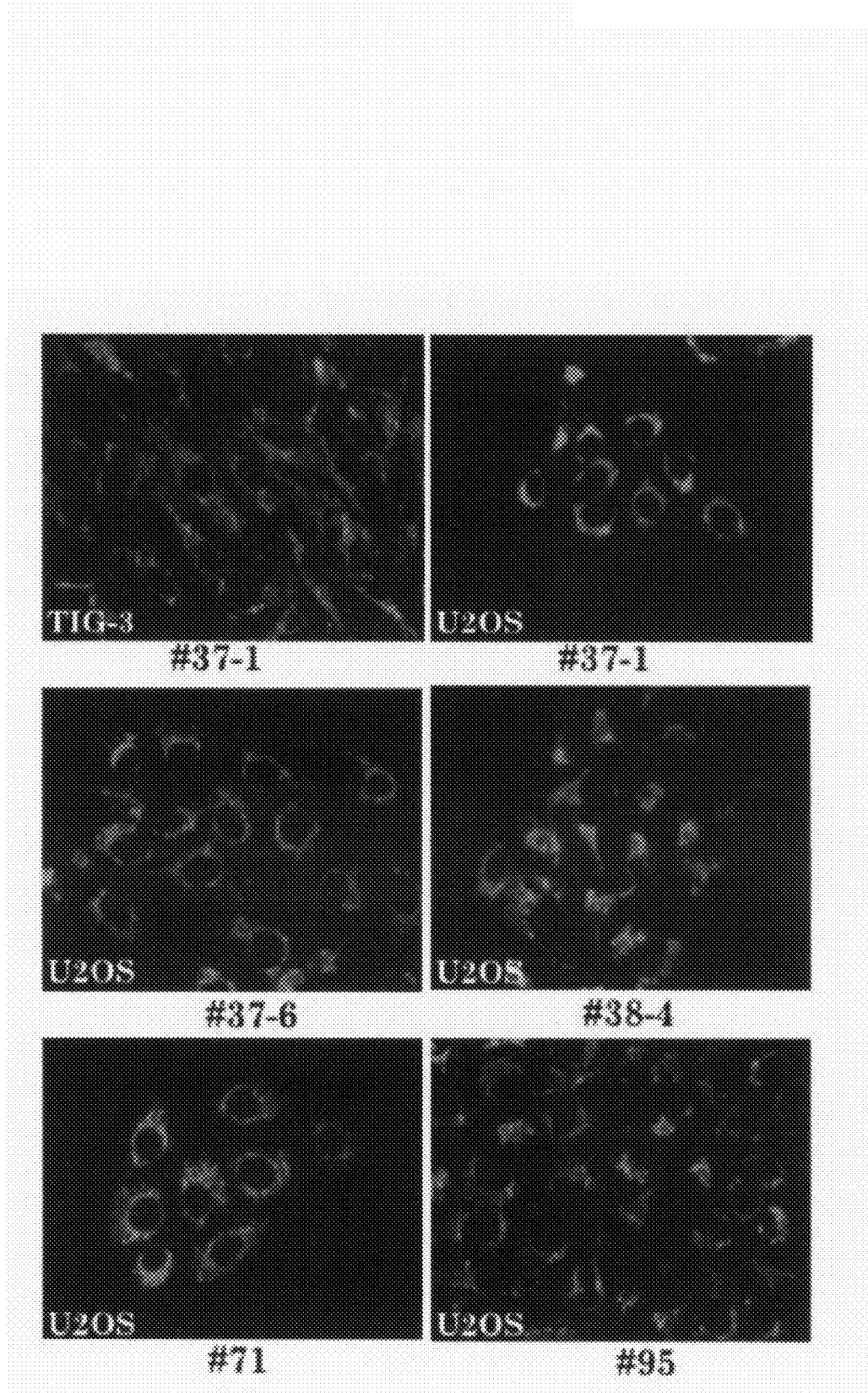
FIG. 34 shows the results of using the anti-mortalin monoclonal antibodies for detecting senescent cells in a cancer cell population (Example 10).
Figure 35:
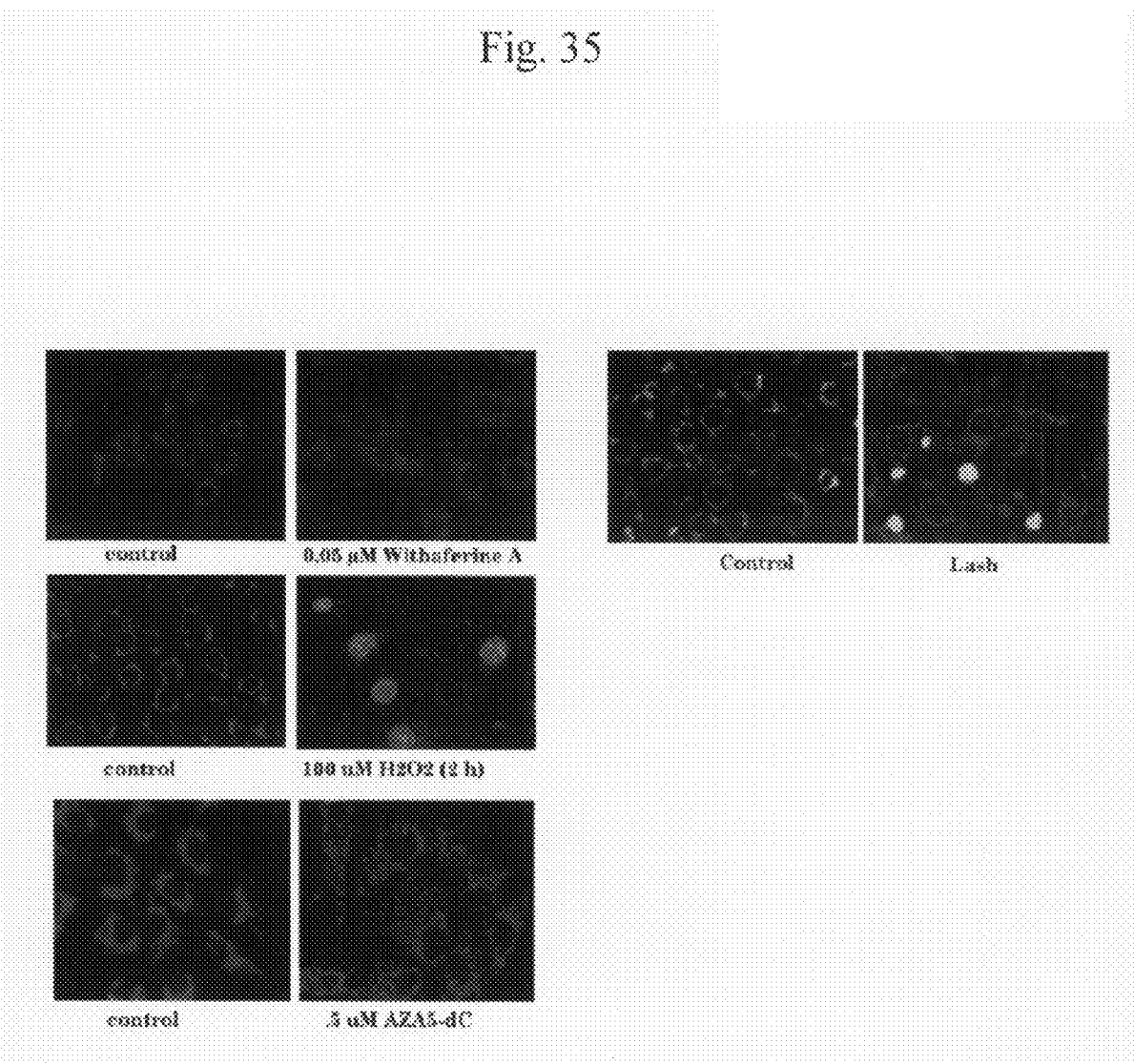
FIG. 35 shows changes in mortalin staining patterns in cancer cells in which senescence has been induced (Example 10).

Immunostaining Patterns of Normal Cells and Cancer Cells with Anti-Mortalin Antibodies Staining patterns were checked using anti-mortalin monoclonal antibodies (FIG. 34) and anti-mortalin polyclonal antibodies (FIG. 35).

FIG. 34 shows the results of use of anti-mortalin monoclonal antibodies for detecting senescent cells in a cancer cell population. Normal cells (TIG-1) and cancer cells (U2OS) were subjected to immunostaining with the use of anti-mortalin monoclonal antibodies.

As shown in FIG. 34, staining was widely observed throughout the cytoplasm in the cases of normal cells. However, in the cases of cancer cells, staining was observed around the nucleus. Such difference in staining patterns was also observed when polyclonal antibodies were used.

FIG. 35 shows the changes in mortalin staining patterns in the cases of cancer cells in which senescence was induced. Senescence was induced in cancer cells with the use of a phytochemical such as Withaferin A (which is a component contained in a crude extract of Ashwagandha), hydrogen peroxide, or azacytidine. Cells were immobilized after drug treatment, followed by immunostaining of mortalin with anti-mortalin polyclonal antibodies (K antibodies).

In the cases of cells in which senescence was induced (in which senescence was confirmed based on cell growth arrest and p53 induction (portions stained green in FIG. 35)), patterns in which mortalin staining was concentrated around the nuclear envelope were replaced with patterns in which mortalin staining was diffused throughout the cytoplasm (portions stained red in FIG. 35).

Example 11

Figure 36:
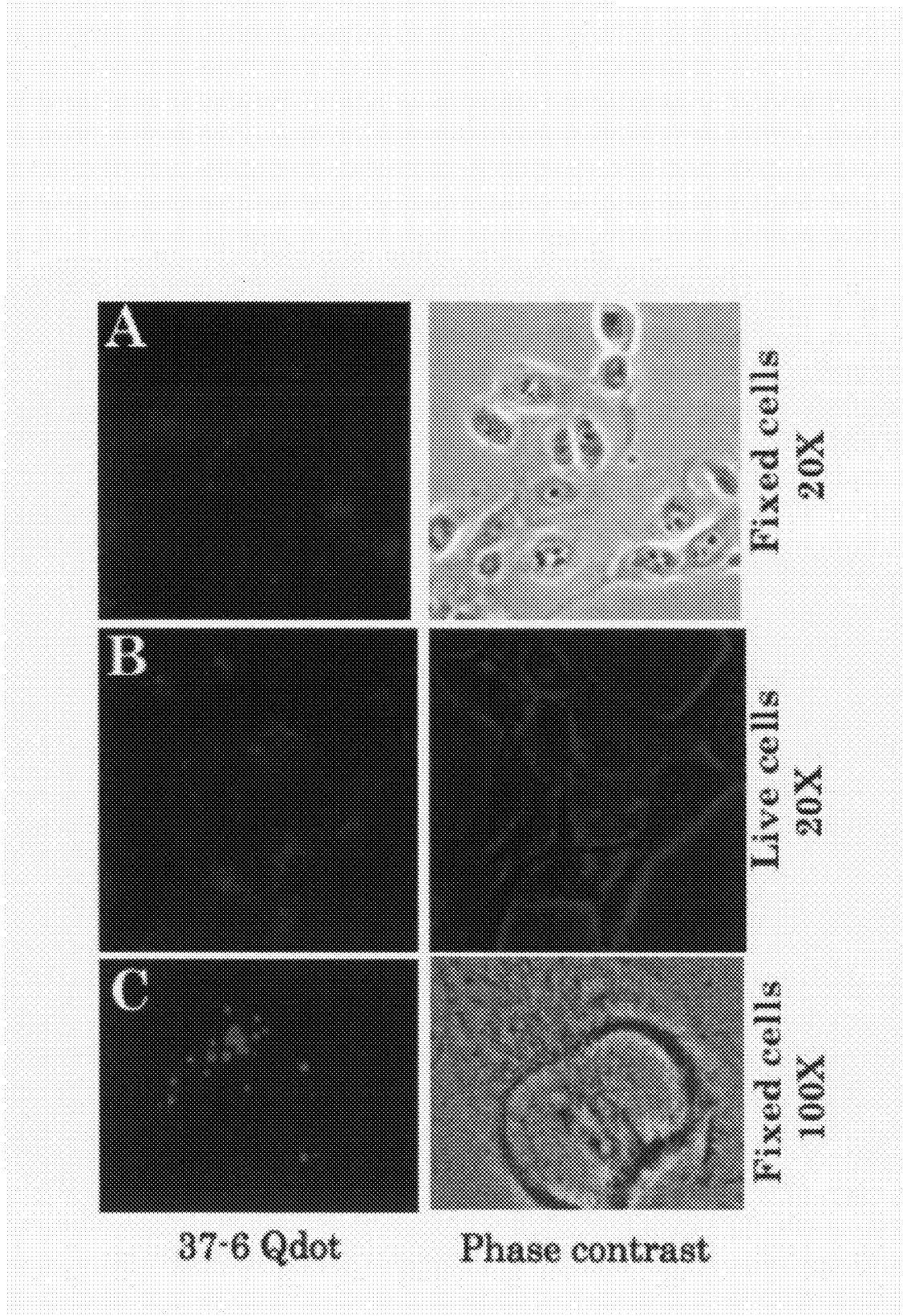
FIG. 36 shows live images with anti-mortalin monoclonal antibodies (Example 11).

Experiment of Live Imaging of Cells with Qdot Using an Anti-Mortalin Monoclonal Antibody as a Carrier FIG. 36 shows live images with an anti-mortalin monoclonal antibody.

Cancer cells (U2OS) were cultured in the presence of anti-mortalin monoclonal antibodies (37-6) bound to Qdots (quantum dots). After 24-hour culture, the cells were divided into the following two types of cases followed by visualization of intracellular antibodies: cases in which cells were immobilized; and cases in which cells were not immobilized. In addition, the anti-mortalin monoclonal antibodies bound to Qdots were removed, and then cells were allowed to cause cell division once or twice, followed by immobilization, and Qdots were then observed.

Results

The anti-mortalin monoclonal antibodies bound to Qdots were intracellularly internalized. Even after cell division, cells remained Qdot-labeled.

INDUSTRIAL APPLICABILITY

The present inventors have revealed that mortalin is involved in cell division control and is closely related to tumor growth. Mortalin is useful as a new target for cancer therapies. With the use of a mortalin-neutralizing substance, it becomes possible to provide new means that can be used for cancer therapies.

FREE TEXT OF SEQUENCE LISTING

<210> 1
<223> Antigen P
<210> 2
<223> Antigen Q
<210> 3
<223> Antigen R
<210> 4
<223> Antigen S
<210> 5
<223> Antigen T
<210> 6
<223> human heat shock 70 kDa protein 9B (mortalin 2) (HSPA9B) (nuclear gene encoding mitochondrial protein) ACCESSION NM_004134
<210> 7
<223> IL-1R type 1 target site
<210> 8
<223> shRNA
<210> 9
<223> IL-1R type 1 target site
<210> 10
<223> shRNA

SEQUENCE LISTING

```
<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<223> OTHER INFORMATION: antigen P

<400> SEQUENCE: 1
```

```
Met Ile Ser Ala Ser Arg Ala Ala Ala Arg Leu Val Gly Thr Ala
1               5                   10                  15

Ala Ser Arg Ser Cys
            20
```

<210> SEQ ID NO 2
<211> LENGTH: 12
<212> TYPE: PRT
<213> ORGANISM: Artificial Sequence
<220> FEATURE:
<223> OTHER INFORMATION: antigen Q

<400> SEQUENCE: 2

```
Cys Gln Gly Glu Arg Glu Met Ala Gly Asp Asn Lys
1               5                   10
```

<210> SEQ ID NO 3
<211> LENGTH: 14
<212> TYPE: PRT
<213> ORGANISM: Artificial Sequence
<220> FEATURE:
<223> OTHER INFORMATION: antigen R

<400> SEQUENCE: 3

```
Cys Glu Glu Ile Ser Lys Val Arg Ala Leu Leu Ala Arg Lys
1               5                   10
```

<210> SEQ ID NO 4
<211> LENGTH: 14
<212> TYPE: PRT
<213> ORGANISM: Artificial Sequence
<220> FEATURE:
<223> OTHER INFORMATION: antigen S

<400> SEQUENCE: 4

```
Cys Glu Glu Ile Ser Lys Met Arg Ala Leu Leu Ala Gly Lys
1               5                   10
```

<210> SEQ ID NO 5
<211> LENGTH: 19
<212> TYPE: PRT
<213> ORGANISM: Artificial Sequence
<220> FEATURE:
<223> OTHER INFORMATION: antigen T

<400> SEQUENCE: 5

```
Ser Gln Val Phe Ser Thr Ala Ala Asp Gly Gln Thr Gln Val Glu Ile
1               5                   10                  15

Lys Val Cys
```

<210> SEQ ID NO 6
<211> LENGTH: 679
<212> TYPE: PRT
<213> ORGANISM: Homo sapiens
<220> FEATURE:
<223> OTHER INFORMATION: Heat shock 70kDa protein 9B (mortalin-2)

<400> SEQUENCE: 6

```
Met Ile Ser Ala Ser Arg Ala Ala Ala Ala Arg Leu Val Gly Ala Ala
1               5                   10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45
```

-continued

```
Glu Ala Ile Lys Gly Ala Val Gly Ile Asp Leu Gly Thr Thr Asn
 50                  55                  60

Ser Cys Val Ala Val Met Glu Gly Lys Gln Ala Lys Val Leu Glu Asn
 65                  70                  75                  80

Ala Glu Gly Ala Arg Thr Thr Pro Ser Val Val Ala Phe Thr Ala Asp
                 85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285

Glu Phe Lys Arg Glu Thr Gly Val Asp Leu Thr Lys Asp Asn Met Ala
    290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
        355                 360                 365

Ala Met Gln Asp Ala Glu Val Ser Lys Ser Asp Ile Gly Glu Val Ile
    370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Asp Val Thr Pro Leu Ser Leu Gly Ile Glu
        435                 440                 445

Thr Leu Gly Gly Val Phe Thr Lys Leu Ile Asn Arg Asn Thr Thr Ile
    450                 455                 460
```

```
Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
            485                 490                 495

Asn Lys Leu Leu Gly Gln Phe Thr Leu Ile Gly Ile Pro Pro Ala Pro
        500                 505                 510

Arg Gly Val Pro Gln Ile Glu Val Thr Phe Asp Ile Asp Ala Asn Gly
    515                 520                 525

Ile Val His Val Ser Ala Lys Asp Lys Gly Thr Gly Arg Glu Gln Gln
530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
        595                 600                 605

Asn Lys Leu Lys Glu Glu Ile Ser Lys Met Arg Glu Leu Leu Ala Arg
    610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675

<210> SEQ ID NO 7
<211> LENGTH: 19
<212> TYPE: RNA
<213> ORGANISM: Artificial Sequence
<220> FEATURE:
<223> OTHER INFORMATION: IL-1R type 1 target site

<400> SEQUENCE: 7
acaagccucc aggauucau                                                  19

<210> SEQ ID NO 8
<211> LENGTH: 51
<212> TYPE: RNA
<213> ORGANISM: Artificial Sequence
<220> FEATURE:
<223> OTHER INFORMATION: shRNA

<400> SEQUENCE: 8
acaagucucu aggauucaug ugugcugucc augaauccug gaggcuuguu u              51

<210> SEQ ID NO 9
<211> LENGTH: 19
<212> TYPE: RNA
<213> ORGANISM: Artificial Sequence
<220> FEATURE:
<223> OTHER INFORMATION: IL-1R type 1 target site

<400> SEQUENCE: 9
gccuccagga uucaucaac                                                  19
```

```
-continued

<210> SEQ ID NO 10
<211> LENGTH: 51
<212> TYPE: RNA
<213> ORGANISM: Artificial Sequence
<220> FEATURE:
<223> OTHER INFORMATION: IL-1R type 1 target site

<400> SEQUENCE: 10
gcuuucagga uucaucaacg ugugcugucc guugaugaau ccuggaggcu u            51
```

The invention claimed is:

1. An anti-mortalin-2 monoclonal antibody produced by hybridoma FERM BP-10408 which can be internalized by live cells.

2. A method of treating cancer, comprising administering to a subject in need thereof an anticancer agent comprising as an active ingredient the anti-mortalin-2 monoclonal antibody of claim 1.

3. A method for transferring a small molecule into cells, comprising contacting the cells with a complex of the small molecule conjugated to the anti-mortalin-2 monoclonal antibody according to claim 1.

4. A kit for targeting a therapeutic agent having anticancer activity, comprising the anti-mortalin-2 monoclonal antibody according to claim 1, wherein said antibody is conjugated to the therapeutic agent.

5. A kit for live imaging of cancer cells, comprising the anti-mortalin-2 monoclonal antibody according to claim 1, and a nonfluorescent or fluorescent substance.

6. A method of examining cancer metastasis, comprising administering to a subject in need thereof the anti-mortalin-2 monoclonal antibody according to claim 1 conjugated to a nonfluorescent or fluorescent visualizing substance.

7. A method for detecting senescent or normalized cells in a cancer cell population or detecting cancer cells in a senescent or normalized cell population, comprising contacting live cells with the anti-mortalin-2 monoclonal antibody according to claim 1, wherein the presence of anti-mortalin-2 throughout the cytoplasm indicates senescent or normalized cells, and wherein the presence of anti-mortalin-2 at the nuclear envelope indicates cancer cells.

8. A kit for detecting senescent or normalized cells in a cancer cell population or for detecting cancer cells in a senescent or normalized cell population, comprising the anti-mortalin-2 monoclonal antibody according to claim 1, a live imaging reagent, and instructions.

9. A method for screening for a substance that transforms cancer cells into senescent or normalized cells comprising contacting a test substance with cancer cells, carrying out live imaging of the cancer cells with the anti-mortalin-2 monoclonal antibody according to claim 1, and observing live imaging patterns, wherein the presence of anti-mortalin-2 throughout the cytoplasm indicates that the test substance transforms cancer cells into senescent or normalized cells.

10. A kit for screening for a substance that transforms cancer cells into a senescent or normalized cells, comprising the anti-mortalin-2 monoclonal antibody according to claim 1, a live imaging reagent, and instructions.

11. An artificial antibody, which is a monomer of an antigen recognition site of the anti-mortalin-2 monoclonal antibody produced by hybridoma FERM BP-10408 or of a peptide that contains said antigen recognition site, or a multimer of said monomer, wherein the artificial antibody can be internalized by live cells.

12. An artificial chimeric antibody, comprising an antigen recognition site of the anti-mortalin-2 monoclonal antibody produced by hybridoma FERM BP-10408 or a peptide that contains said antigen recognition site, and an antibody that recognizes another antigen, a part of said antibody that recognizes another antigen, or a protein, wherein the artificial chimeric antibody can be internalized by live cells.

13. A complex comprising a small molecule drug and a delivery substance for said drug, wherein the small molecule drug and the delivery substance are conjugated to an antigen recognition site of the anti-mortalin-2 monoclonal antibody produced by hybridoma FERM BP-10408 or a peptide that contains said antigen recognition site, wherein the complex can be internalized by live cells.

14. A method for detecting senescent or normalized cells in a cancer cell population or detecting cancer cells in a senescent or normalized cell population, comprising immunostaining cells with the anti-mortalin-2 monoclonal antibody produced by hybridoma FERM BP-10408 that specifically binds to mortalin-2, wherein the presence of anti-mortalin-2 immunostaining throughout the cytoplasm indicates senescent or normalized cells, and wherein the presence of anti-mortalin-2 immunostaining at the nuclear envelope indicates cancer cells.

15. A kit for detecting senescent or normalized cells in a cancer cell population or for detecting cancer cells in a senescent or normalized cell population, comprising the anti-mortalin-2 monoclonal antibody produced by hybridoma FERM BP-10408 an immunostaining reagent, and instructions.

16. A method for screening for a substance that transforms cancer cells into senescent or normalized cells comprising contacting a test substance with cancer cells, immunostaining the cancer cells with the anti-mortalin-2 monoclonal antibody produced by FERM BP-10408 that specifically binds to mortalin-2, and observing immunostaining patterns, wherein the presence of anti-mortalin-2 throughout the cytoplasm indicates that the test substance transforms cancer cells into senescent or normalized cells.

17. A kit for screening for a substance that transforms cancer cells into a senescent or normalized cells, comprising the anti-mortalin-2 monoclonal antibody produced by hybridoma FERM BP-10408 an immunostaining reagent, and instructions.

* * * * *